US010329486B2

(12) United States Patent
Bury S. Pires et al.

(10) Patent No.: US 10,329,486 B2
(45) Date of Patent: Jun. 25, 2019

(54) CYANOSTILBENES

(71) Applicant: ROLIC AG, Zug (CH)

(72) Inventors: Izabela Bury S. Pires, Allschwil (CH); Sabrina Chappellet, Village-Neuf (FR); Mohammed Ibn-Elhaj, Allschwil (CH); Frederic Lincker, Schiltigheim (FR)

(73) Assignee: ROLIC AG, Zug (CH)

( * ) Notice: Subject to any disclaimer, the term of this patent is extended or adjusted under 35 U.S.C. 154(b) by 68 days.

(21) Appl. No.: 14/888,960

(22) PCT Filed: May 22, 2014

(86) PCT No.: PCT/EP2014/060508
§ 371 (c)(1),
(2) Date: Nov. 4, 2015

(87) PCT Pub. No.: WO2014/191292
PCT Pub. Date: Dec. 4, 2014

(65) Prior Publication Data
US 2016/0083655 A1 Mar. 24, 2016

(30) Foreign Application Priority Data
May 28, 2013 (EP) .................... 13169419

(51) Int. Cl.
C09K 19/56 (2006.01)
C07C 255/37 (2006.01)
C09K 19/16 (2006.01)
C09D 179/08 (2006.01)
C08G 73/10 (2006.01)
G02F 1/1337 (2006.01)
C07C 255/38 (2006.01)
C08F 120/18 (2006.01)
C08F 220/18 (2006.01)
C08G 73/12 (2006.01)
C09K 19/04 (2006.01)

(52) U.S. Cl.
CPC ............ *C09K 19/56* (2013.01); *C07C 255/37* (2013.01); *C07C 255/38* (2013.01); *C08F 120/18* (2013.01); *C08F 220/18* (2013.01); *C08G 73/1075* (2013.01); *C08G 73/1078* (2013.01); *C08G 73/124* (2013.01); *C09D 179/08* (2013.01); *C09K 19/16* (2013.01); *G02F 1/133711* (2013.01); *G02F 1/133788* (2013.01); *C09K 2019/0448* (2013.01); *C09K 2019/161* (2013.01); *G02F 2001/133726* (2013.01); *Y10T 428/1005* (2015.01); *Y10T 428/1014* (2015.01); *Y10T 428/1023* (2015.01)

(58) Field of Classification Search
CPC ............ C09K 19/56; C09K 2019/0496; G02F 1/133711; C07D 255/41; C07D 317/46; C07D 319/08; Y10T 428/1005; Y10T 428/1014; Y10T 428/1018; Y10T 428/1023
USPC ..... 428/1.2, 1.25, 1.26, 1.27, 1.28; 349/123, 349/127; 524/549, 548; 558/402
See application file for complete search history.

(56) References Cited

U.S. PATENT DOCUMENTS

| 6,107,427 A | 4/2000 | Herr et al. |
| 2008/0274304 A1 | 11/2008 | Cherkaoui et al. |
| 2014/0192305 A1 | 7/2014 | Lincker et al. |
| 2014/0249244 A1 | 9/2014 | Chappellet et al. |

FOREIGN PATENT DOCUMENTS

| WO | 2007/033506 A1 | 3/2007 |
| WO | 2013/026691 A1 | 2/2013 |
| WO | 2013/050121 A1 | 4/2013 |

OTHER PUBLICATIONS

Jeonghwan Lee et al., "Polarized Light Emission in a Liquid Crystalline Copolymer Film Comprised of Fluorenevinylene and Photo-Cross-Linkable Mesogenic Side Groups", Mol. Cryst. Liq. Cryst., 2010, vol. 529, pp. 20-24.
A.M. Ahmed et al., "A new class of main-chain liquid crystalline polymers based on an unsymmetrically distributed cyanostilbene", Polymer, 1993, pp. 1297-1302, vol. 34, No. 6.
Takashi Mihara et al., "Synthesis and Thermal Properties of Combined Liquid Crystalline Epoxy Resins", Journal of Applied Polymer Science, 1998, pp. 1979-1990, vol. 68.
S.J. Martin et al., "Linear Electro-optic Effect in a New Class of Main Chain Liquid Crystalline Polymers", Organic Materials for Non-Linear Optics III, 1993, pp. 295-299.
International Search Report for PCT/EP2014/060508 dated Jun. 26, 2014.
Written Opinion for PCT/EP2014/060508 dated Jun. 26, 2014.

*Primary Examiner* — Ruiyun Zhang
(74) *Attorney, Agent, or Firm* — Sughrue Mion, PLLC

(57) ABSTRACT

The present invention relates to novel compounds that are particularly useful for the alignment, especially photoalignment, of slave material, especially liquid crystals for optical or electro-optical applications, such as security applications, liquid crystal devices or optical or electro-optical films.

18 Claims, No Drawings

CYANOSTILBENES

CROSS REFERENCE TO RELATED APPLICATIONS

This application is a National Stage of International Application No. PCT/EP2014/060508 filed May 22, 2014, claiming priority based on European Patent Application No. 13169419.2 filed May 28, 2013, the contents of all of which are incorporated herein by reference in their entirety.

The present invention relates to compounds that are particularly useful for the alignment, especially photoalignment, of slave material, especially liquid crystals for optical or electro-optical applications, such as security applications, liquid crystal devices or optical or electro-optical films.

The photoalignment process for the orientation of slave material, especially liquid crystals, is a very economic and ecologic way of manufacturing because it generates nearly any wastage.

Hence, there is a constant growing demand from the market to provide further photoalignment material having advanced properties for the desired application, such as high contrast, good alignment quality, azimuthal stability or high speed of orientation.

Thus, the present invention relates in a first aspect to compounds according to the general formula (I)

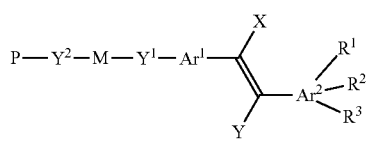

preferably

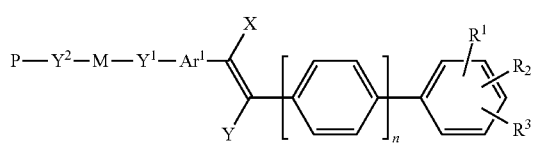

wherein
Ar$^1$ and Ar$^2$ are independently from each other a ring system of 4 to 40 atoms, wherein each ring system includes at least one unsaturation directly connected via electron conjugation (π-π bonding) to the double bond shown in formula (I),
wherein the ring system is unsubstituted or mono- or poly-substituted by a halogen atom and/or a polar group like hydroxy, nitro, nitrile, —CF$_3$; or by a carboxy group, and/or a cyclic, straight-chain or branched alkyl residue having from 1 to 30 carbon atoms, which is unsubstituted, mono- or poly-substituted by methyl, fluorine and/or chlorine, wherein one or more, preferably non-adjacent —CH$_2$— groups independently may be replaced by a group selected from —O—, —CO—, —CO—O—, —O—CO—, —NR$^{1'}$—, —NR$^{1'}$—CO—, —CO—NR$^{1'}$—, —NR$^{1'}$—CO—O—, —O—CO—NR$^{1'}$—, —NR$^{1'}$—CO—N R$^{1'}$—, —CH═CH—, —C≡C—, —O—CO—O— and —Si(CH$_3$)$_2$—O—Si(CH$_3$)$_2$—, an aromatic or an alicyclic group, wherein R$^{1'}$ is a hydrogen atom or lower alkyl; and/or an acryloyloxy, alkoxy, alkylcarbonyloxy, alkyloxocarbonyloxy, methacryloyloxy, vinyl, allyl, vinyloxy and/or allyloxy group, having from 1 to 20 carbon atoms, preferably having from 1 to 10 carbon atoms; preferably the ring system is unsubstituted or substituted by an alkoxy group; and wherein;
if X is hydrogen and Y is CN,
then R$^1$, R$^2$ or R$^3$ are independently from each other hydrogen, halogen or —CF$_3$, with the proviso that R$^1$, R$^2$ or R$^3$ are not simultaneously hydrogen;
if X is CN and Y is hydrogen;
then R$^1$, R$^2$ or R$^3$ are independently from each other hydrogen, halogen or —CF$_3$;
M is a single covalent bond or a spacer unit;
Y$^1$, Y$^2$ are independently from each other a bridging group, n is 0, 1, 2 or 3; preferably 0,
P is a hydrogen atom, optionally substituted alkyl, or a polymerizable group.

In the context of the present application, a "slave material" shall refer to any material that has the capability to establish anisotropy upon contact with a photo-aligned material. The nature of the anisotropy in the photo-aligned material and in the slave material may be different from each other. For example, the slave material may exhibit light absorption anisotropy for visible light and therefore can act as a polarizer, whereas the anisotropy of the photo-aligned material may only be related to the molecular orientation. There may be also moieties of the photo-alignable material, for example in a co-polymer, which are not sensitive to aligning light, but create anisotropic properties because of interaction with the photo-sensitive moieties, which undergo a photo-reaction upon exposure to aligning light. Such a material exhibits properties of a photo-alignable material and of a slave material, but shall be included in the meaning of a photo-alignable material.

A slave material may comprise polymerizable and/or non-polymerizable compounds. Within the context of the present application the terms "polymerizable" and "polymerized" shall include the meaning of "cross-linkable" and "cross-linked", respectively. Likewise, "polymerization" shall include the meaning of "cross-linking".

Preferably, the slave material is a self organizing material. More preferred is that the slave material is a liquid crystal material and in particular preferred is that the slave material is a liquid crystal polymer material.

A liquid crystal polymer (LCP) material as used within the context of this application shall mean a liquid crystal material, which comprises liquid crystal monomers and/or liquid crystal oligomers and/or liquid crystal polymers and/or cross-linked liquid crystals. In case the liquid crystal material comprises liquid crystal monomers, such monomers may be polymerized, typically after anisotropy has been created in the LCP material due to contact with a photo-aligned material. Polymerization may be initiated by thermal treatment or by exposure to actinic light, which preferably, comprises uv-light. A LCP-material may consist of a single type of liquid crystal compound, but may also be a composition of different polymerizable and/or non-polymerizable compounds, wherein not all of the compounds have to be liquid crystal compounds. Further, an LCP material may contain additives, for example, a photo-initiator or isotropic or anisotropic fluorescent and/or non-fluorescent dyes.

In the context of this application, an alignment layer comprising compound (I), as a photo-alignable material, is also referred to as a light controlled molecular orientation (LCMO) layer, no matter if it has already been exposed to polarized light or not. Accordingly, an LCMO layer, as used herein, may have no anisotropic property as long as it has not been exposed to aligning light, preferably polarized light and has anisotropic property after it has been exposed to aligning light. Typically, an LCMO layer may be a thin layer applied to a substrate. It is also possible that the LCMO layer is thick and mechanically stable enough, such that it can be handled without an additional substrate. In the latter case, the LCMO layer has also the function of a substrate.

In the context of the present application, the term "aligning light" shall mean light, which can induce anisotropy in a photo-alignable material and which is at least partially linearly or elliptically polarized. Preferably, the aligning light is linearly polarized with a degree of polarization of more than 5:1. Wavelengths, intensity and energy of the aligning light are chosen depending on the photosensitivity of the photo-alignable material. Typically, the wavelengths are in the UV-A, UV-B and/or UV-C range or in the visible range. Preferably, the aligning light comprises light of wavelengths less than 450 nm. More preferred is that the aligning light comprises light of wavelengths less than 420 nm.

If the aligning light is linearly polarized, the polarization plane of the aligning light shall mean the plane defined by the propagation direction and the polarization direction of the aligning light. In case the aligning light is elliptically polarized, the polarization plane shall mean the plane defined by the propagation direction of the light and by the major axis of the polarization ellipse.

In a further aspect, the compound (I) is part of an oligomer, dendrimer, or polymer. In the context of the present invention the term polymer is a homopolymer or a copolymer and/or an oligomer and/or dendrimer. Said polymer may be obtained by polymerization of the monomer of general formula (I) and may be in form of a gel or a network.

The invention relates in a further aspect to alignment layer materials comprising said compounds according to formula (I) in monomeric, oligomeric, dendrimeric or polymeric form. Such alignment layer materials are particularly useful for the alignment of liquid crystals and polymerizable, dimerizable or crosslinkable liquid crystalline materials.

The invention relates in yet a further aspect to optical elements, e.g. polymerized, dimerized or crosslinked films having a nematic, smectic or cholesteric order, and electro-optical elements, e.g. liquid crystal display cells, comprising an alignment layer made of a material comprising a compound according to the general formula (I) in monomeric, oligomeric, dendrimeric or polymeric form.

In specific embodiments, the alignment layer has a pattern of different alignment directions, which pattern advantageously can be formed by photoalignment methods.

In a further aspect the invention also relates to the use of materials containing a compound according to formula (I) for the preparation of alignment layers.

It is understood that the wording "each ring system includes at least one unsaturation directly connected via electron conjugation (π-π bonding) to the double bond" indicates that each ring system $Ar^1$ and $Ar^2$ contains at least one unsaturated bond, i.e. double bond, that is directly linked to the double bond in formula (I) thereby extending the electron conjugation.

In a preferred embodiment ring systems $Ar^1$ an $Ar^2$ is a carbocyclic or heterocyclic ring group selected from a monocyclic ring of four to six atoms, or two adjacent monocyclic rings of five or six atoms, or a fused bicyclic ring system of eight, nine or ten atoms, or a fused tricyclic ring system of thirteen or fourteen atoms. More preferably ring systems $Ar^1$ and $Ar^2$ are selected from pyrimidine, pyridine, thiophenylene, furanylene, phenanthrylene, naphthylene, biphenylene or phenylene. Most preferred $Ar^1$ is phenylene, which is unsubstituted or substituted with —O-methyl, preferably $Ar^1$ is unsubstituted. Further most preferred $Ar^2$ is phenylene or biphenylene, preferably phenylene, which is unsubstituted or substituted by $R^1$, $R^2$ and $R^3$ within the above given meanings and preferences.

In a further preferred embodiment of the present invention the bridging group is a group selected from but not limited to a single bond, —O—, —CO—, —CO—O—, —O—CO—, —NR$^{1'}$—, —NR$^{1'}$—CO—, —CO—, NR$^{1'}$—, —NR$^{1'}$—CO—O—, —O—CO—NR$^{1'}$—, —NR$^{1'}$—CO—N R$^{1'}$—, —CH=CH—, —C≡C—, —O—CO—O— and —Si(CH$_3$)$_2$—O—Si(CH$_3$)$_2$—, wherein R$^{1'}$ is a hydrogen atom or lower alkyl, preferably single bond, —O—, —CO—, —COO—, —OCO—, —CH=CH—, —C≡C—. More preferably $Y^1$ and $Y^2$ are single bond, —O—, —CO—, —COO—, —OCO—, and most preferred $Y^1$ is —O— and $Y^2$ is single bond, —O—, —CO—, —COO— or —OCO—.

In a further preferred embodiment M is a single bond or a straight-chain or branched alkylene residue having 1, 2, 3, 4, 5, 6, 7, 8, 9, 10, 11, 12, 13, 14, 15, 16, 17, 18, 19, 20, 21, 22, 23 or 24, preferably 1, 2, 3, 4, 5, 6, 7, 8, 9, 10, 11, 12, 13, 14, 15 or 16, more preferably 6, 7, 8, 9, 10, 11 or 12 carbon atoms, most preferred 8, 9, 10 or 11, which is unsubstituted, mono-substituted by cyano or halogen, or poly-substituted by halogen and wherein one or more, preferably non-adjacent CH$_2$ groups independently may be replaced by a heteroatom or a group selected from but not limited to —O—, —CO—, —CO—O—, —O—CO—, —NR$^{1'}$—, —NR$^{1'}$—CO—, —CO—, NR$^{1'}$—, —NR$^{1'}$—CO—O—, —O—CO—NR$^{1'}$—, —NR$^{1'}$—CO—N R$^{1'}$—, —CH=CH—, —C≡C—, —O—CO—O— and —Si(CH$_3$)$_2$—O—Si(CH$_3$)$_2$—, preferably selected from —O—, —CO—, —COO—, —OCO—, —CH=CH—, —C≡C—, wherein R$^{1'}$ is a hydrogen atom or lower alkyl. Preferably M is unsubstituted.

In a further preferred embodiment the polymerizable group in P is selected from unsubstituted or substituted acrylate, methacrylate, 2-chloroacrylate, 2-phenylacrylate, optionally N-lower alkyl substituted acrylamide, methacrylamide, 2-chloroacrylamide, 2-phenylacrylamide, vinyl ether and ester, allyl ether and ester, epoxy, carbonic acid ester, acetal, styrene and styrene derivatives, for example alpha-methylstyrene, p-methylstyrene, p-tert-butyl styrene, p-chlorostyrene, etc., siloxanes, silane, diamine, imide monomers, amic acid monomers and their esters, amidimide monomers, maleic acid and maleic acid derivatives, for example, di-n-butyl maleate, dimethyl maleate, diethyl maleate, etc, maleinimide, norbornene, norbornene derivatives, fumaric acid and fumaric acid derivatives, for example, di-n-butyl fumarate, di-(2-ethylhexyl) fumarate, etc, urea, urethanes or their corresponding homo- and co-polymers and mixtures thereof. More preferably the polymerizable group in P is selected from acrylate, methacrylate, vinyl ether and ester, epoxy, styrene derivatives, siloxanes, imide monomers, amic acid monomers and their corresponding polymers, homo or copolymers.

In a yet a further embodiment
$Ar^1$ is a ring system of formula (II):

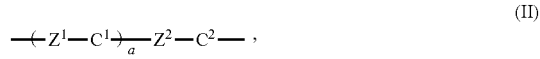

(II)

and
Ar² is a ring system of formula (IIa)

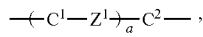
(IIa)

wherein:
C¹, C² each independently are a non-aromatic or aromatic, optionally substituted, carbocyclic or heterocyclic group of 5 to 14 atoms, preferably connected to each other at the opposite positions via the bridging groups Z¹ and Z²,
Z¹, Z² each independently are a single bond or a bridging group preferably selected from —CH(OH)—, —O—, —CH₂(CO)—, —SO—, —CH₂(SO)—, —SO₂—, —CH₂(SO₂)—, —COO—, —OCO—, —COF₂—, —CF₂CO—, —S—CO—, —CO—S—, —SOO—, —OSO—, —CH₂—CH₂—, —O—CH₂—, —CH₂O—, —CH=CH—, —C≡S—, —SH=CH—COO—, —OCO—CH=CH—, —CH=N—, —C(CH₃)=N—, —O—CO—O—, —N=N—, or a short alkyl spacer of 1 to 6 carbon atoms, preferably 1 to 3 carbon atoms,
a is 0, 1, 2 or 3, with the proviso that C², which is directly connected to the double bond, is unsaturated and conjugated to it.

The term "connected to each other at the opposite positions via the bridging groups Z¹ and Z²" means that five- and six-membered rings are preferably linked in 1,3- or 1,4-position. Analogous linking pattern in other e.g. higher membered rings will be obvious to a skilled person.

Preferably C¹, C² in formula (II) independently have one of the following meanings:

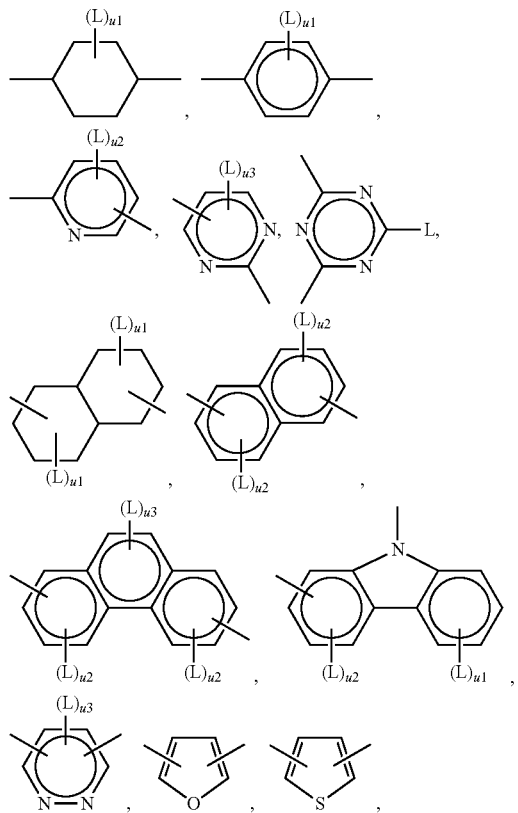

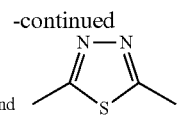
and wherein
L is halogen, hydroxyl, and/or a polar group such as nitro, cyano or carboxy, and/or acryloyloxy, alkoxy, such as methoxy, ethoxy, propoxy, alkylcarbonyloxy, alkyloxocarbonyloxy, methacryloyloxy, vinyl, vinyloxy, allyl, allyloxy, and/or a cyclic, straight-chain or branched alkyl residue, which is unsubstituted, mono- or poly-substituted by fluorine and/or chlorine, and/or a silane group, and/or a siloxane group, wherein the alkyl residue has from 1 to 20 C-atoms, wherein one or more, preferably non-adjacent, —CH₂— groups independently may be replaced by a group, preferably selected from —O—, —CO—, —COO—, —OCO—, —CH=CH—, —C≡C—, —Si(CH₃)₂—, —Si(CH₃)₂—O—Si(CH₃)₂—, preferably L is methoxy
u1 is 0, 1, 2, 3, or 4, preferably 0 or 1,
u2 is 0, 1, 2, or 3, preferably 0 or 1, and
u3 is 0, 1, or 2 preferably 0 or 1,
with the proviso that C², which is directly connected to the double bond, is unsaturated and conjugated to it.

More preferably C¹, C² are phenanthryl or phenanthrylene, biphenyl or biphenylene, naphthyl or naphthylene, phenyl or phenylene, pyridine or pyridinylene; preferably naphthyl or naphthylene, phenyl or phenylene, pyridine or pyridinylene, and more preferably phenyl or phenylene.

Preferably L is selected from akoxy, more preferably methoxy, ethoxy or propoxy.

Preferably Z¹, Z² in formulae (II) and (III) each independently are a single bond or a bridging group selected from —CH(OH)—, —O—, —CH₂(CO)—, —COO—, —OCO—, —COF₂—, —CF₂CO—, —CH₂—CH₂—, —O—CH₂—, —CH₂O—, —CH=CH—, —OCO—CH=CH—, —CH=N—, —C(CH₃)=N—, —O—CO—O—, —N=N—, or a short alkyl spacer of 1 to 6 carbon atoms, preferably 1 to 3 carbon atoms.

More preferably Z¹, Z² each independently are a single bond —O—, —CH₂(CO)—, —COO—, —OCO—, —CH₂—CH₂—, —OCO—CH=CH—, —N=N—, or a short alkyl spacer of 1 to 3 carbon atoms.

Preferred compounds of formula (I) are those, wherein Ar¹ is a ring system of formula (II):

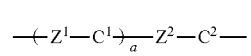
(II)

and
Ar² is a ring system of formula (IIa)

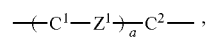
(IIa)

wherein:
C¹, C² each independently are a non-aromatic or aromatic, optionally substituted, carbocyclic or heterocyclic group of 5 to 14 atoms, preferably connected to each other at the opposite positions via the bridging groups Z¹ and Z², $Z^1$, $Z^2$ each independently are a single bond or a bridging group preferably selected from —CH(OH)—, —O—, —CH$_2$(CO)—, —SO—, —CH$_2$(SO)—, —SO$_2$—, —CH$_2$(SO$_2$)—, —COO—, —OCO—, —COF$_2$—, —CF$_2$CO—, —S—CO—, —CO—S—, —SOO—, —OSO—, —CH$_2$—CH$_2$—, —O—CH$_2$—, —CH$_2$O—, —CH=CH—, —C≡S—, —SH=CH—OCO—, —OCO—CH=CH—, —CH=N—, —C(CH$_3$)=N—, —O—CO—O—, —N=N—, or a short alkyl spacer of 1 to 6 carbon atoms, preferably 1 to 3 carbon atoms, a is 0, 1, 2 or 3, preferably a is 0 or 1, more preferably 0, with the proviso that $C^2$, which is directly connected to the double bond, is unsaturated and conjugated to it;

or more preferred are compounds of formula (Ia), wherein and wherein;

if X is hydrogen and Y is CN, then $R^1$, $R^2$ or $R^3$ are independently from each other hydrogen, halogen or —CF$_3$ with the proviso that $R^1$, $R^2$ or $R^3$ are not simultaneously hydrogen;

or preferably, if X is hydrogen and Y is CN, then $R^1$ is fluoro, chloro, bromo or —CF$_3$, and $R^2$ and $R^3$ are hydrogen; or $R^1$ and $R^2$ is independently from each other fluoro, chloro, bromo or —CF$_3$, and $R^3$ is hydrogen; or $R^1$, $R^2$ or $R^3$ are simultaneously flouro, chloro or bromo; or if X is CN and Y is hydrogen;

then $R^1$ is fluoro, chloro, bromo or —CF$_3$, and $R^2$ and $R^3$ are hydrogen; or $R^1$ and $R^2$ is independently from each other fluoro, chloro, bromo or —CF$_3$, and $R^3$ is hydrogen; or $R^1$, $R^2$ or $R^3$ are simultaneously hydrogen, flouro, chloro or bromo;

M is a single bond or a straight-chain or branched alkylene residue having 1, 2, 3, 4, 5, 6, 7, 8, 9, 10, 11, 12, 13, 14, 15, 16, 17, 18, 19, 20, 21, 22, 23 or 24, preferably 1, 2, 3, 4, 5, 6, 7, 8, 9, 10, 11, 12, 13, 14, 15 or 16, more preferably 6, 7, 8, 9, 10, 11 or 12 carbon atoms, most preferred 8, 9, 10 or 11, wherein one or more —CH$_2$— groups independently may be replaced by a group selected from —O—, —CO—, —COO—, —OCO—, —CH=CH—, —C≡C—;

P is a hydrogen atom, optionally substituted alkyl, or a polymerizable group.

Thus more preferred compounds are compounds according to formula (I) wherein $Ar^1$ is a ring system of formula (II):

(II)

and $Ar^2$ is a ring system of formula (IIa)

(IIa)

wherein:

$C^1$, $C^2$ each independently are phenyl or phenylene;

$Z^1$, $Z^2$ each independently are a single bond or —O—, —CH$_2$(CO)—, —COO—, —OCO—, —CH$_2$—CH$_2$—, —OCO—CH=CH—, —N=N—, or a short alkyl spacer of 1 to 3 carbon atoms, a is 0 or 1, preferably 0;

or most preferred are compounds of formula (Ia);

and wherein;

if X is hydrogen and Y is CN, then $R^1$, $R^2$ or $R^3$ are independently from each other hydrogen, halogen or —CF$_3$ with the proviso that $R^1$, $R^2$ or $R^3$ are not simultaneously hydrogen;

or preferably, if X is hydrogen and Y is CN, then $R^1$ is fluoro, chloro, bromo or —CF$_3$, and $R^2$ and $R^3$ are hydrogen; or $R^1$ and $R^2$ is independently from each other fluoro, chloro, bromo or —CF$_3$, and $R^3$ is hydrogen; or $R^1$, $R^2$ or $R^3$ are simultaneously flouro, chloro or bromo; or if X is CN and Y is hydrogen;

then $R^1$ is fluoro, chloro, bromo or —CF$_3$, and $R^2$ and $R^3$ are hydrogen; or $R^1$ and $R^2$ is independently from each other fluoro, chloro, bromo or —CF$_3$, and $R^3$ is hydrogen; or $R^1$, $R^2$ or $R^3$ are simultaneously hydrogen, flouro, chloro or bromo;

M is a single bond or a straight-chain or branched alkylene residue having 1, 2, 3, 4, 5, 6, 7, 8, 9, 10, 11, 12, 13, 14, 15, 16, 17, 18, 19, 20, 21, 22, 23 or 24, preferably 1, 2, 3, 4, 5, 6, 7, 8, 9, 10, 11, 12, 13, 14, 15 or 16, more preferably 6, 7, 8, 9, 10, 11 or 12 carbon atoms, most preferred 8, 9, 10 or 11, wherein one or more —CH$_2$— groups independently may be replaced by a group selected from —O—, —COO—, —OCO—, —CH=CH—;

P is a hydrogen atom, optionally substituted alkyl, or a polymerizable group selected from acrylate, methacrylate, vinyl ether and ester, epoxy, siloxanes, silane, diamines, imide monomers, amic acid monomers and their ester, and mixtures thereof, or their corresponding homo- and co-polymers.

The term "alkyl", unless the context requires otherwise, includes straight-chain and branched alkyl, as well as saturated and unsaturated groups.

The term "lower alkyl", as used in the context of the present invention, taken on its own or in a combination such us "lower alkoxy", etc., preferably denotes straight-chain and branched saturated hydrocarbon groups having from 1 to 6, preferably from 1 to 3, carbon atoms. Methyl, ethyl, propyl and isopropyl groups are especially preferred. In case of "lower alkoxy", methoxy, ethoxy, propoxy and isopropoxy groups are especially preferred.

The term "aliphatic", unless the context requires otherwise, includes straight-chain and branched alkyl, as well as saturated and unsaturated groups. Possible substituents include alkyl, aryl (thus giving an araliphatic group) and cycloalkyl, as well as amino, cyano, epoxy, halogen, hydroxy, nitro, oxo etc. Possible heteroatoms which may replace carbon atoms include nitrogen, oxygen and sulphur. In the case of nitrogen further substitution is possible with groups such as alkyl, aryl and cycloalkyl.

The term "alicylic", as used in the context of the present invention, preferably denotes optionally substituted non-aromatic carbocyclic or heterocyclic ring systems, with 3 to 30 carbon atoms, e.g. cyclopropane, cyclobutane, cyclopentane, cyclopentene, cyclohexane, cyclohexene, cyclohexadiene, decaline, tetrahydrofuran, dioxane, pyrrolidine, piperidine or a steroidal skeleton such as cholesterol.

The term "aromatic", as used in the context of the present invention, preferably denotes optionally substituted carbocyclic and heterocyclic aromatic groups, incorporating five, six, ten or 14 ring atoms, e.g. furan, benzene, pyridine, pyrimidine, naphthalene, phenanthrene, biphenylene or tetraline units.

The term "phenylene", as used in the context of the present invention, preferably denotes a 1,2-, 1,3- or 1,4-phenylene group, which is optionally substituted. It is preferred that the phenylene group is either a 1,3- or a 1,4-phenylene group. 1,4-phenylene groups are especially preferred.

The term "halogen" denotes a chloro, fluoro, bromo or iodo substituent, preferably a chloro or fluoro substituent.

The term "polar group", as used in the context of the present invention primarily denotes a group like hydroxy, nitro, nitrile, —$CF_3$ or a carboxy group.

The term "heteroatom", as used in the context of the present invention primarily denotes oxygen, sulphur and nitrogen, preferably oxygen and nitrogen, in the latter case preferably in the form of —NH—.

The term "optionally substituted" as used in the context of the present invention primarily means substituted by lower alkyl, lower alkoxy, hydroxy, halogen or by a polar group as defined above.

With respect to straight or branched alkyl, alkylene, alkoxy, alkoxycarbonyl, alkylcarbonyl, alkylcarbonyloxy groups it is repeatedly pointed out that some or several of the —$CH_2$— groups may be replaced e.g. by heteroatoms, but also by other groups. In such cases it is generally preferred that such replacement groups are not directly linked to each other. It is alternatively preferred that heteroatoms, and in particular oxygen atoms are not directly linked to each other.

The term "polymerizable group" as used in the context of the present invention refers to a functional group that can be subjected to polymerization (optionally with other comonomers) to yield an oligomer, dendrimer or polymer according to the present invention. For a person skilled in the art it will be obvious which functional groups are intended for any specific polymer. Thus for example in case of "imid monomer" as the indicated polymer backbone group it is obvious to a person skilled in the art that the actual monomer units for polymerization to yield a polyimid are e.g. diamines and dianhydrides. Similarly regarding "urethane monomer" the actual monomer units are diols and diisocyanates.

The compounds according to the present invention in form of prefinished monomers may be readily prepared using methods that are well known to the person skilled in the art. Suitable methods can for instance be found in Houben-Weyl, Methoden der Organischen Chemie, Thieme-Verlag, Stuttgart.

Subsequently these prefinished monomers are typically subjected to direct polymerisation to obtain an oligomer, dendrimer or polymer. Thus, the compounds of the present invention may also be part of an oligomer, a dendrimer or a polymer, which may be a homopolymer or a copolymer.

In a specific embodiment the compounds of formula (I) may be formulated with any other monomers, functional moieties and additives.

For the direct polymerisation, the monomers and (optionally) the comonomers are firstly prepared separately from the individual components. Subsequently the formation of the polymers is effected in a manner known per se for any given polymer for example under the influence of UV radiation or heat or by the action of radical or ionic catalysts. Potassium peroxodisulfate, dibenzoyl peroxide, azobisisobutyronitrile or di-tert-butyl peroxide are examples of radical initiators. Ionic catalysts are alkali-organic compounds such as phenyllithium or naphthylsodium or Lewis acids such as $BF_3$, $AlCl_3$, $SnCl_3$ or $TiCl_4$. The monomers can be polymerised in solution, suspension, emulsion or substance.

If copolymerized with other comonomers the obtained copolymers are consisting of a monomer unit derivating from formula (I) as defined in any of the proceeding meanings and any other known monomer unit that is commercially available or not.

Upon polymerization it may further be advantageous to terminate the growing polymer chain after a suitable chain length is reached by capping the polymerizable group present at the chain end by using specific reagents well known in the art.

Suitable polymers include polyacrylates, polymethacrylates, polyacrylamides, polymethacrylamides, polyvinylether and polyvinylester, polyallylether and ester, polystyrenes, polysiloxanes, polyimides, polyamic acids and their esters, polyamidimides, polymaleic acids, polyfumaric acids polyurethanes or derivatives thereof or mixtures thereof.

These polymers may all be prepared according to well known methods in the art. Thus for example the poly(meth) acrylates described herein may be prepared in line with methods such as described in Polymer Synthesis Characterization: A Laboratory Manual (Stanley R. Sandler, Wolf Karo, JoAnne Bonesteel, Eli M. Pearce) and Principles of Polymerization (George Odian).

Thus in the case when the monomer unit is bearing an acrylic or methacrylic end, the comonomer unit can be represented by compounds listed below. Most of them are commercially available from chemical suppliers such as Aldrich, ABCR, ACROS, Fluka.

2,2,2-trifluoroethyl acrylate, 2-hydroxyethyl acrylate, acrylic acid, glycidyl acrylate, methyl acrylate, tert-butyl acrylate, ethyl acrylate, butyl acrylate, 2-ethylhexyl acrylate, 3-sulfopropyl acrylate, potassium salt, 4-hydroxybutyl acrylate, 2-bromoethyl acrylate, 2-cyanoethyl acrylate, tetrahydrofurfuryl acrylate, allyl acrylate, stearyl acrylate, 2-(2-ethoxyethoxy)ethyl acrylate, 2-hydroxypropyl acrylate, isohexadecyl acrylate, 2-tetrahydrofuryl acrylate, n,n-dimethylaminoethyl acrylate, 1h,1h-perfluorooctyl acrylate, 1h,1h-heptafluorobutyl acrylate, 2,2,3,3,3-pentafluoropropyl acrylate, 1h,1h,5h-octafluoropentyl acrylate, 1,1,1,3,3,3-hexafluoroisopropyl acrylate, d,l-menthyl acrylate, beta-carboxyethyl acrylate, 1h,1h,11h-eicosafluoroundecyl acrylate, 2-fluoroethyl acrylate, 1h,1h,2h,2h-perfluorodecyl acrylate, pentafluorobenzyl acrylate, pentafluorophenyl acrylate, 1h,1h,2h,2h-perfluorooctyl acrylate, 2,2,3,3-tetrafluoropropyl acrylate, isobutyl acrylate, lauryl acrylate, n,n-diethylaminoethyl acrylate, 2-ethoxyethyl acrylate, (r)-(+)-alpha-acryloyloxy-beta,beta-dimethyl-gamma-butyrolactone, 2,2,3,4,4,4-hexafluorobutyl acrylate, 2-chloroethyl acrylate, cyclohexyl acrylate, methallyl acrylate, phenyl acrylate, acrylic anhydride, benzyl acrylate, 2-methoxyethyl acrylate, cinnamyl acrylate, 3-methoxybutyl acrylate, iso-propyl acrylate, n-decyl acrylate, undecyl acrylate, tridecyl acrylate, 2-ethylbutyl acrylate, n-propyl acrylate, acryloxytri-n-butyltin, 2-n-butoxyethyl acrylate, n-amyl acrylate, n-hexyl acrylate, n-heptyl acrylate, n-octyl acrylate, 2-hydroxy-3-chloropropyl acrylate, 2-phenoxyethyl acrylate, iso-amyl acrylate, sec-butyl acrylate, n-(3-acryloxy-2-hydroxypropyl)-3-aminopropyltriethoxysilane, (3-acryloxypropyl)methylbis(trimethylsiloxy)silane, (3-acryloxypropyl)dimethylmethoxy-silane, 3-acryloxypropyl tris(trimethylsiloxy)silane, (3-acryloxypropyl) trimethoxysilane, (3-acryloxypropyl)methyldichlorosilane, (3-acryloxypropyl)trichlorosilane, vinyl acrylate, 2,3-dibromopropyl acrylate, mono-(acryloyloxyethyl) phthalate, 3-acryloxypropyl-2-n-phenyl carbamate, 2-hydroxy-3-phenoxypropyl acrylate, potassium acrylate, sodium acrylate, [2-(acryloyloxy)ethyl](4-benzoylbenzyl)dimethylammonium bromide, n-acryloxysuccinimide, 1h,1h,9h-hexadecafluorononyl acrylate, 3,3,5-trimethylcyclohexyl acrylate, n-nonyl acrylate, cyclopentyl acrylate, perfluorooctyl acrylate, 2-allyloxyethoxyethyl acrylate, crotyl acrylate, 4-cumylphenyl acrylate, 2,4,6-tribromophenyl acrylate, hexadecyl acrylate, propargyl acrylate, acrylate, ammonium, acrylate, cesium, lithium acrylate, acrylate, rubidium, n-(acryloxyethyl) phthalimide, n-(acryloxyethyl) succinimide, mono-2-acryloyloxyethyl maleate, 2-allyloxyethyl acrylate allyloxypropyl acrylate, behenyl acrylate, 1,3-bis(4-benzoyl-3-hydroxyphenoxy)-2-propyl acrylate, isobornyl acrylate, 2-(bromo-1-naphthyloxy)-ethyl acrylate, 2-(1-bromo-2-naphthyloxy)-ethyl acrylate, p-chlorophenoxyethyl acrylate, 4-chlorophenyl acrylate, 2-cyanoethoxyethyl acrylate, cyclol acrylate, iso-decyl acrylate, dibutyltin acrylate, n,n-diethylaminoethyl acrylate q-salt, methosulfate, [2-(acryloyloxy)ethyl]trimethylammonium chloride, 3,6-dioxaheptyl acrylate, furfuryl acrylate, 2,3-dihydroxypropyl acrylate, hexoxyethyl acrylate, 3-iodobenzyl acrylate, d-menthyl acrylate, 1-menthyl acrylate, 2-methyl butyl acrylate, 2-n-morpholinoethyl acrylate, alpha-naphthyl acrylate, beta-naphthyl acrylate, 2-(1-naphthyloxy)-ethyl acrylate, 2-(2-naphthyloxy)-ethyl acrylate, 2-nitroethyl acrylate, p-nitrophenyl acrylate, nonylphenyl acrylate, norbornyl acrylate, 2-octyl acrylate, isooctyl acrylate, pentabromophenyl acrylate, pentachlorophenyl acrylate, neo-pentyl acrylate, (perfluorocyclohexyl)methyl acrylate, 2-phenylethyl acrylate, phenylpropyl acrylate, mono-2-acryloyloxyethyl phthalate, 1-piperidineethyl acrylate, silver acrylate, sorbitol acrylate, trichloroethyl acrylate, [2-(acryloyloxy)ethyl]trimethylammonium methyl sulphate, 3,5,5-trimethylhexyl acrylate vinylbenzyl acrylate, 2-(n-butylperfluorooctanesulfamido)ethyl acrylate, 2-(n-ethylperfluorooctanesulfamido) ethyl acrylate, 3-(trifluoromethyl)benzyl acrylate, 1h,1h,7h-dodecafluoroheptyl acrylate, 3-dimethylamino neopentyl acrylate, 1h,1h,3h-hexafluorobutyl acrylate, 2-(4-benzoyl-3-hydroxyphenoxy)ethyl acrylate, monoacryloxyethyl phosphate, 2,2-dinitropropyl acrylate, abitol acrylate, potassium acrylate, hemihydrate, 2-(acryloxyethoxy)trimethylsilane, (3-acryloxypropyl)methyldimethoxysilane, Acryloxytrimethylsilane, acryloxytriphenyltin, sodium acrylate, hemihydrate, dicyclopentenyl acrylate, dicaprolactone 2-(acryloyloxy)ethyl ester, di(ethylene glycol) 2-ethylhexyl ether acrylate, dicyclopentenyloxyethyl acrylate, 3-(dimethylamino)propyl acrylate, 4,4-dimethyl-2-oxotetrahydrofuran-3-yl acrylate, 2-(perfluorobutyl)ethyl acrylate, 3-(perfluorobutyl)-2-hydroxypropyl acrylate, 3-(perfluorohexyl)-2-hydroxypropyl acrylate, 3-(perfluorooctyl)-2-hydroxypropyl acrylate, 2-(perfluorodecyl)ethyl acrylate, 2-(perfluoro-3-methylbutyl)ethyl acrylate, 3-(perfluoro-3-methylbutyl)-2-hydroxypropyl acrylate, 2-(perfluoro-5-methylhexyl)ethyl acrylate, 2-(perfluoro-9-methyloctyl) ethyl acrylate, 2-(perfluoro-9-methyldecyl)ethyl acrylate, urethane acrylate, mono-2-(acryloyloxy)ethyl succinate, heptafluoro-2-propyl acrylate, (3-(allanoyloxy)-5-[4-(benzoylamino)-2-oxopyrimidin-1(2h)-yl]tetrahydrofuran-2-y, dihydrodicyclopentadienyl acrylate, 2-(acryloyloxy)ethyl acetoacetate acrylic acid 3-(1-oxo-1,3-dihydro-isoindol-2-yl)-phenyl ester, 4-tert-butylcyclohexyl acrylate, acrylic acid 3-(3,5-dioxo-4-aza-tricyclo(5.2.1.0(2,6))dec-8-en-4-yl)-ph ester, acrylic acid 3-(4-nitro-1,3-dioxo-1,3-dihydro-isoindol-2-yl)-phenyl ester, acrylic acid 3-(4,5,6,7-tetrachloro-1, 3-dioxo-1,3-2h-isoindol-2-yl)-phenyl ester methyl furyl acrylate, rcl r35,845-2, acrylic acid 3-(2,5-dioxo-pyrrolidin-1-yl)-phenyl ester, acrylic acid 3-(1,3-dioxo-1,3-dihydro-isoindol-2-yl)-phenyl ester, cobalt acrylate, manganese acrylate, 3-acryloyloxypropyl-2-n-phenyl carbamate, acrylated bisphenol "a" glycidyl ether, 3-(perfluoro-5-methylhexyl)-2-hydroxypropyl acrylate, 3-(perfluoro-7-methyloctyl)-2-hydroxypropyl acrylate, neopentyl glycol acrylate benzoate, 2'-cinnamoyloxyethyl acrylate, triisopropylsilyl acrylate, uvecryl p 36, 2-[[(butylamino)carbonyl]oxy]ethyl acrylate, 1h,1h-perfluoro-n-decyl acrylate, methacrylic acid, 2-hydroxyethyl methacrylate, 2-hydroxypropyl methacrylate, glycidyl methacrylate, methacrylic anhydride, methyl methacrylate, 2-(dimethylamino)ethyl methacrylate, allyl methacrylate, 3-methacryloxypropyltrimethoxysilane, isobutyl methacrylate, lauryl methacrylate, ethyl methacrylate, 2-ethoxyethyl methacrylate, n-butyl methacrylate, 2-ethylhexyl methacrylate, potassium sulfopropylmethacrylate, 2,2,2-trifluoroethyl methacrylate, cyclohexyl methacrylate, tetrahydrofurfuryl methacrylate, 2-(tert-butylamino)ethyl methacrylate, n-hexyl methacrylate, 1,6-hexanediol dimethacrylate, 3-methyl-2-benzothiazolinone, azine with 4'(2-(me-acryloyl-o)ethoxy)acetophenone 2-(p-nitrophenoxy) ethyl methacrylate, stearyl methacrylate 2-hydroxy-3-methacryloxypropyl trimethyl ammonium chloride 2-phenylethyl methacrylate, 2-(diethylamino)ethyl methacrylate 1h,1h-perfluorooctyl methacrylate, 1h,1h-heptafluorobutyl methacrylate 2,2,3,3,3-pentafluoropropyl methacrylate, 1h,1h,5h-octafluoropentyl methacrylate 1,1,1,3,3,3-hexafluoroisopropyl methacrylate, n-(3-sulfopropyl)-n-methacryloxyethyl-n,n-dimethylammonium betaine 3-chloro-2-hydroxypropyl methacrylate, d,l-menthyl methacrylate, 1h,1h,11h-perfluoroundecyl methacrylate, 2-fluoroethyl methacrylate, 1h,1h,2h,2h-perfluorodecyl methacrylate, 2,2,3,4,4,4-hexafluorobutyl methacrylate, pentafluorobenzyl methacrylate, pentafluorophenyl methacrylate, 2,2,3,3-tetrafluoropropyl methacrylate, 2-bromoethyl methacrylate, methacrylato chromic chloride, 2-chloroethyl methacrylate, cyclopentyl methacrylate, 1,4-cyclohexanedimethyl 1,4-dimethacrylate,2-cyanoethyl methacrylate, barium methacrylate, potassium methacrylate, magnesium methacrylate, sodium methacrylate, zinc methacrylate, furfuryl methacrylate, phenyl methacrylate, neopentyl glycol dimethacrylate, methallyl methacrylate, 2-methoxyethyl methacrylate, propargyl methacrylate, 3-methoxybutyl methacrylate, tert-butyl methacrylate, iso-propyl methacrylate, iso-amyl methacrylate, n-decyl methacrylate, sec-butyl methacrylate, 2-ethylbutyl methacrylate, n-propyl methacrylate, 2-n-butoxyethyl methacrylate, hydroxypropyl methacrylate, Methacryloxypropylmethyldichlorosilane, benzyl methacrylate, 2-phenoxyethyl methacrylate, methacryloxypropyltris(methoxyethoxy)silane, 3-methacryloxypropyl pentamethyl disiloxane, iso-decyl methacrylate, methacryloxytri-n-butyltin, n-amyl methacrylate, n-octyl methacrylate, trimethylsilyl methacrylate, 2-(trimethylsiloxy)ethyl methacrylate, methacryloxypropylbis(trimethylsiloxy)methylsilane, methacryloxypropyltris (trimethylsiloxy)silane, methacryloxypropyldimethylethoxysilane, 3-methacryloxypropylmethyldiethoxysilane, 3-methacryloxypropyldimethylchlorosilane, 2-methacryloxyethyldimethyl(3-trimethoxysilylpropyl)ammonium chloride, acetoacetoxyethyl methacrylate, methacryloxypropyltrichlorosilane, 3-methacryloxypropyltris(vinyldimethylsiloxy)silane, trimethylsilylmethyl methacrylate, (methacryloxymethyl)phenyldimethylsilane, methacryloxypropenyl trimethoxysilane, methacrylate, calcium, tridecyl methacrylate, vinyl methacrylate, methoxyethoxyethyl methacrylate, [2-(methacryloyloxy)ethyl]trimethylammonium chloride, mono-(2-(methacryloyloxy)-ethyl) phthalate, 2-hydroxy-3- phenoxypropyl methacrylate, methacryloxypropyltriethoxysilane, 2-diisopropylaminoethyl methacrylate, 1h,1h,2h,2h-perfluorooctyl methacrylate, 2-aminoethyl methacrylate hydrochloride 2-trimethylammonium ethyl methacrylate methosulfate, trityl methacrylate perfluorooctyl methacrylate, 2,4,6-tribromophenyl methacrylate, 4-hydroxybutyl methacrylate, hexadecyl methacrylate, undecyl methacrylate, n-nonyl methacrylate, 2-allyloxyethoxyethyl methacrylate, 3,3,5-trimethylcyclohexyl methacrylate, 2,3-dibromopropyl methacrylate, cinnamyl methacrylate, crotyl methacrylate, 1h,1h,9h-hexadecafluorononyl methacrylate, n-heptyl methacrylate 2-allyloxyethyl methacrylate, allyloxy propyl methacrylate, neo-pentyl methacrylate, 2-(1-aziridinyl)-ethyl methacrylate, behenyl methacrylate, 5-norbornene-2-methanol methacrylate, 1,3-bis(4-benzoyl-3-hydroxyphenoxy)-2-propyl methacrylate, ethoxyethoxyethyl methacrylate, p-chlorophenoxyethyl methacrylate, 4-cumylphenyl methacrylate, dibutyltin methacrylate, n,n-diethylaminoethyl methacrylate q-salt, methosulfate, diethylene glycol mono-methacrylate, 2,3-dihydroxypropyl methacrylate, 3,3-dimethyl butanol-2 methacrylate, ethyl triglycol methacrylate, ethylidene dimethacrylate, ethylthioethyl methacrylate, hexoxyethyl methacrylate, 2-(1-imidazoloyl)ethyl methacrylate, 3-iodobenzyl methacrylate, isocyanatoethyl methacrylate, d-menthyl methacrylate l-menthyl methacrylate, aluminum methacrylate, n-(methacryloxyethyl) phthalimide, n-(methacryloxyethyl) succinimide, 4-methacryloxyethyl trimellitic anhydride, 4-methacryloxy-2-hydroxybenzophenone, mono-(2-(methacryloyloxy)-ethyl) maleate, 2-methacryloyloxymethyl-2,3-dihydro-4h-pyran, methoxypropyl methacrylate, 3-methyl butanol-2 methacrylate, 3-methylbuten-2-yl-methacrylate, 2-methyl butyl methacrylate, 3-(4-methylphenoxy)-2-hydroxypropyl methacrylate, 2-n-morpholinoethyl methacrylate, alpha-naphthyl methacrylate, 2-naphthyl methacrylate, 2-(1-naphthyloxy)-ethyl methacrylate, 2-(2-naphthyloxy)-ethyl methacrylate, 2-nitroethyl methacrylate, p-nitrophenyl methacrylate, nonylphenyl methacrylate, norbornyl methacrylate, iso-octyl methacrylate, pentabromophenyl methacrylate, pentachlorophenyl methacrylate, perfluorocyclohexyl methyl methacrylate, phenylpropyl methacrylate, 1-piperidineethyl methacrylate, sorbitol methacrylate, 2-sulfoethyl methacrylate, tribromoneopentyl methacrylate, trichloroethyl methacrylate, 1h,1h,7h-dodecafluoroheptyl methacrylate, 3,5,5-trimethylhexyl methacrylate, methacryloxyethoxy tris(trimethylsiloxy)silane, vinylbenzyl methacrylate, 2-(n-ethylperfluorooctanesulfamido)ethyl methacrylate 3-(trifluoromethyl)benzyl methacrylate, isobornyl methacrylate, poly(ethylene glycol) methacrylate, hydroxypropyl methacrylate, lead methacrylate 2-ethylhexanoate, 2-methacryloxyethyl glucoside, bis-(2,3-dibromopropyl) 2-(methacryloyloxy)-ethyl phosphate, 3-methyl-2-benzothiazolinone, azine with 4-(2-(me-acryloyl-o)eto)-m-anisaldehyde, 2-(methacryloyloxy)ethyl n-(3-bromophenyl)carbamate, 2-(methacryloyloxy)ethyl n-(n-(3,5-dichlorophenyl)carbamoyl)carbamate, 2-(methacryloyloxy)ethyl n-(4-isopropylphenyl)carbamate, ethylene glycol methacrylate phosphate, trimethylol propane diallyl ether mono-methacrylate, abitol methacrylate, isocyanatoethyl methacrylate butyl urethane, isocyanatoethyl methacrylate octyl urethane, isocyanatoethyl methacrylate caprolactam adduct isocyanatoethyl methacrylate pyrrolidone adduct, methacrylic acid hydroxypropyl ester, calcium methacrylate, hydrate, 2-hydroxy-4-[2-hydroxy-3-(methacryloyloxy)-propoxy]benzophen, Methacryloxydiphenylantimony, (2-methacryloxyethoxy) triisopropoxytitanate, (methacryloxymethyl)bis(trimethylsiloxy)methylsilane, (methacryloxymethyl)dimethylethoxysilane, Methacryloxymethyltriethoxysilane, Methacryloxymethyltrimethoxysilane, methacryloxymethyltrimethylgermane, methacryloxymethyltris(trimethylsiloxy)silane, methacryloxypropyldimethylmethoxysilane, methacryloxypropylmethyldimethoxysilane, methacryloxypropylsilatrane, methacryloxytriethylgermane, titanium methacrylate triisopropoxide, dicyclopentenyl methacrylate, tetrahydropyranyl methacrylate, caprolactone 2-(methacryloyloxy)ethyl ester, 2-methyl-2-nitropropyl methacrylate, 2-(2-oxo-1-imidazolidinyl)ethyl methacrylate, tetrakis(2-methacryloxyethoxy)silane 2-(methylthio)ethyl methacrylate, 2-[3-(2h-benzotriazol-2-yl)-4-hydroxyphenyl]ethyl methacrylate, dicyclopentenyloxyethyl methacrylate, 2-methyl-acrylic acid 4-hydroxy-phenyl ester 2-(perfluorobutyl)ethyl methacrylate, 2-(perfluorodecyl)ethyl methacrylate 2-(perfluoro-3-methylbutyl)ethyl methacrylate, 3-(perfluoro-3-methylbutyl)-2-hydroxypropyl methacrylate, 2-(perfluoro-5-methylhexyl)ethyl methacrylate, 3-(perfluoro-5-methylhexyl)-2-hydroxypropyl methacrylate, 2-(perfluoro-7-methyloctyl)ethyl methacrylate, 3-(perfluoro-7-methyloctyl)-2-hydroxypropyl methacrylate, 2-(perfluoro-9-methyldecyl)ethyl methacrylate, 3-(perfluoro-8-methyldecyl)-2-hydroxypropyl methacrylate, (9-anthryl) methacrylate, (9-phenanthryl)methyl methacrylate, n-(3-methacryloxy-2-hydroxypropyl)-3-aminopropyltriethoxysilane, 4-(methacryloyloxy) chalcone, mono-2-(methacryloyloxy)ethyl succinate, 2-(sulfooxy)ethyl methacrylate, ammonium salt, ethylene methacrylate phosphate, 2-me-acrylic acid 2-(4-(1,3-dioxo-1,3-dihydro-isoindol-2-yl)-phenyl)-ethyl ester, 2-(2'-methacryloxy-5'-methylphenyl)benzotriazole, 2-me-acrylic acid 3(3,5-dioxo-4-azatricyclo(5.2.1.0(2,6))dec-8-en-4-yl)ph ester, 2-me-acrylic acid 4-(4-nitro-1,3-dioxo-1,3-dihydro-isoindol-2-yl)-phenyl ester, rcl r35,715-4, 9-anthracenylmethyl methacrylate, 1-pyrenylmethyl methacrylate, 2-methyl-acrylic acid 3-(1-oxo-1,3-dihydro-isoindol-2-yl)-phenyl ester, 2-me-acrylic acid 3-(4-nitro-1,3-dioxo-1,3-dihydro-isoindol-2-yl)-phenyl ester, 2-methyl-acrylic acid 3-(2,5-dioxo-pyrrolidin-1-yl)-phenyl ester, 2-methyl-acrylic acid 4-(2,5-dioxo-pyrrolidin-1-yl)-phenyl ester, rcl r35,836-3, 2-methyl-acrylic acid 4-acetylamino-phenyl ester, (1-pyrene)methyl methacrylate, 2-hydroxypropyl 2-(methacryloyloxy)ethyl phthalate, peg monomethacrylate, 3-methylbuten-2-yl-1-methacrylate, (methacryloxymethyl)bis(trimethylsiloxy)-(methylsiloxy)methylsilane, (r)-2-hydroxy-2'-methacryloxy-1,1'-bi-2-naphthol, 4-[[6-(methacryloyloxy)hexyl]oxy]benzenecarboxylic acid, hexafluoroisopropyl urethane of isocyanato ethyl methacrylate, dicyclopentenyl-2-methacrylate, (r)-(–)-isobornylmethacrylate, 3-perfluorohexyl-2-hydroxypropyl methacrylate, 3-perfluorooctyl-2-hydroxypropyl methacrylate, (1-naphthyl)ethyl methacrylate, (1-naphthyl)methyl methacrylate, o-methacryloyl hoechst 33258, o-(methacryloxyethyl)-n-(triethoxysilylpropyl) urethane, 4-[3-(methacryloyloxy)propoxy]benzenecarboxylic acid, 4-[4-(methacryloyloxy)butoxy]benzenecarboxylic acid, hexafluoroisopropylurethane-n-ethyl methacrylate, 2-methyl-acrylic acid 2-(4-(4,5-dihydro-oxazol-2-yl)-phenoxy)-ethyl ester, 3-methacryloxypropyltris(pentamethyldisiloxy)silane, di(propylene glycol) allyl ether methacrylate, triacetoneaminoylmethacrylate, 1h,1h-perfluoro-n-decyl methacrylate, 3-(perfluorobutyl)-2-hydroxypropyl methacrylate, 2-methyl-acrylic acid 4-(3-phenyl-acryloyl)-phenyl ester, 3-(5-nitro-1,3-dioxo-1,3-dihydro-2h-isoindol-2-yl)phenyl 2-methylacrylate, n-(2-hydroxy-3((2-methyl-1-oxo-2-propenyl)oxy)propyl)-n-(4-methylphenyl)-glycine or mixtures thereof.

The polyamic acids, polyamic acid esters and polyimides according to the present invention may be prepared in line with known methods, such as those described in Plast. Eng. 36 (1996), (Polyimides, fundamentals and applications), Marcel Dekker Inc. For example, the polycondensation reaction for the preparation of the polyamic acids is carried out in solution in a polar aprotic organic solvent, such as γ-butyrolactone, N,N-dimethylacetamide, N-methylpyrrolidone or N,N-dimethylformamide. In most cases equimolar amounts of the dianhydride and the diamine are used, that is to say one amino group per anhydride group. If it is desired to stabilise the molecular weight of the polymer, it is possible for that purpose to add an excess or a less-than-stoichiometric amount of one of the two components or to add a monofunctional compound in the form of a dicarboxylic acid monoanhydride or in the form of a monoamine. Examples of such monofunctional compounds are maleic anhydride, phthalic anhydride, aniline and so on. The reaction is carried out preferably at a temperature of less than 100° C.

The cyclisation of the polyamic acids to form the polyimides can be carried out by heating, that is to say by condensation with removal of water or by other imidisation reactions with reagents. When carried out purely thermally, the imidisation of the polyamic acids is not always complete, that is to say the resulting polyimides may still contain proportions of polyamic acid. The imidisation reactions are generally carried out at a temperature of from 60 to 250° C., but preferably at less than 200° C. In order to achieve imidisation at rather lower temperatures there are additionally mixed into the reaction mixture reagents that facilitate the removal of water. Such reagents are, for example, mixtures consisting of acid anhydrides, such as acetic acid anhydride, propionic acid anhydride, phthalic acid anhydride, trifluoroacetic acid anhydride, and tertiary amines, such as triethylamine, trimethylamine, tributylamine, pyridine, N,N-dimethylaniline, lutidine, collidine etc. The amount of reagents used in that case is preferably at least two equivalents of amine and four equivalents of acid anhydride per equivalent of polyamic acid to be condensed.

The imidisation reaction can be carried out before or alternatively only after application to a support. The latter variant is preferred especially when the polyimide in question has poor solubility in the customary solvents.

Thus the polymer material or oligomer material from the class of polyamic acids, polyamic acid esters or polyimides (and any mixtures thereof) may be obtained by or obtainable by the reaction of at least one compound represented by the general formula (I) wherein G represents a diamine group and optionally one or more additional other diamines (as e.g. given above), with one or more tetracarboxylic acid anhydrides of the general formula (IV)

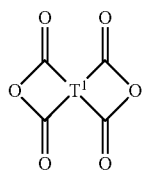

(IV)

wherein:
$T^1$ represents a tetravalent organic radical.

The tetravalent organic radical $T^1$ is preferably derived from an aliphatic, alicyclic or aromatic tetracarboxylic acid dianhydride.

Preferred examples of aliphatic or alicyclic tetracarboxylic acid dianhydrides are:
1,1,4,4-butanetetracarboxylic acid dianhydride,
ethylenemaleic acid dianhydride,
1,2,3,4-cyclobutanetetracarboxylic acid dianhydride,
1,2,3,4-cyclopentanetetracarboxylic acid dianhydride,
2,3,5-tricarboxycyclopentylacetic acid dianhydride,
3,5,6-tricarboxynorbornylacetic acid dianhydride,
2,3,4,5-tetrahydrofurantetracarboxylic acid dianhydride,
rel-[1S,5R,6R]-3-oxabicyclo[3.2.1]octane-2,4-dione-6-spiro-3'-(tetrahydrofuran2',5'-dione),4-(2,5-dioxotetrahydrofuran-3-yl)tetrahydronaphthalene-1,2-dicarboxylicacid dianhydride, 5-(2,5-dioxotetrahydrofuran-3-yl)-3-methyl-3-cyclohexene-1,2-dicarboxylic-acid dianhydride, bicyclo[2.2.2]oct-7-ene-2,3,5,6-tetracarboxylic acid dianhydride,
bicyclo[2.2.2]octane-2,3,5,6-tetracarboxylic acid dianhydride,
1,8-dimethylbicyclo[2.2.2]oct-7-ene-2,3,5,6-tetracarboxylic acid dianhydride, and the like.

Preferred examples of aromatic tetracarboxylic acid dianhydrides are:
pyromellitic acid dianhydride,
3,3',4,4'-benzophenonetetracarboxylic acid dianhydride,
4,4'-oxydiphthalic acid dianhydride,
3,3',4,4'-diphenylsulfonetetracarboxylic acid dianhydride,
1,4,5,8-naphthalenetetracarboxylic acid dianhydride,
2,3,6,7-naphthalenetetracarboxylic acid dianhydride,
3,3',4,4'-dimethyldiphenylsilanetetracarboxylic acid dianhydride,
3,3',4,4'-tetraphenylsilanetetracarboxylic acid dianhydride,
1,2,3,4-furantetracarboxylic acid dianhydride,
4,4'-bis(3,4-dicarboxyphenoxy)diphenyl sulfide dianhydride,
4,4'-bis(3,4-dicarboxyphenoxy)diphenyl sulfone dianhydride,
4,4'-bis(3,4-dicarboxyphenoxy)diphenylpropane dianhydride,
3,3',4,4'-biphenyltetracarboxylic acid dianhydride,
ethylene glycol bis(trimellitic acid) dianhydride,
4,4'-(1,4-phenylene)bis(phthalic acid) dianhydride,
4,4'-(1,3-phenylene)bis(phthalic acid) dianhydride,
4,4'-(hexafluoroisopropylidene)diphthalic acid dianhydride,
4,4'-oxydi(1,4-phenylene)bis(phthalic acid) dianhydride,
4,4'-methylenedi(1,4-phenylene)bis(phthalic acid) dianhydride,
and the like.

More preferably the tetracarboxylic acid dianhydrides used to form the tetravalent organic radical $T^1$ are selected from:
1,2,3,4-cyclobutanetetracarboxylic acid dianhydride,
1,2,3,4-cyclopentanetetracarboxylic acid dianhydride,
2,3,5-tricarboxycyclopentylacetic acid dianhydride,
5-(2,5-dioxotetrahydrofuran-3-yl)-3-methyl-3-cyclohexene-1,2-dicarboxylic acid dianhydride,
4-(2,5-dioxotetrahydrofuran-3-yl)tetrahydronaphthalene-1,2-dicarboxylic acid dianhydride,
4,4'-(hexafluoroisopropylidene)diphthalic acid dianhydride and bicyclo[2.2.2]oct-7-ene-2,3,5,6-tetracarboxylic acid dianhydride.

The term "diamine" or "diamine compound" is to be understood as designating a chemical structure which has at least two amino groups, i.e. which may also have 3 or more amino groups.

The diamine represents an optionally substituted aliphatic, aromatic or alicyclic diamino group having from 1 to 40 carbon atoms and preferably made from or selected from the following group of structures: aniline, p-phenylenediamine, m-phenylenediamine, benzidine, diaminofluorene, or their derivatives, with the proviso that compounds listed which do not carry two amino groups are taken as derivatives with at least one additional amino group, and more preferably made from or selected from the following commercially available amino compounds (example of suppliers: Aldrich, ABCR, ACROS, Fluka) which can also be used as comonomers:

4-amino-2,3,5,6-tetrafluorobenzoic acid
4-amino-3,5-diiodobenzoic acid, 3,4-diaminobenzoic acid
4-amino-3-methylbenzoic acid,
4-amino-2-chlorobenzoic acid
4-aminosalicylic acid
4-aminobenzoic acid
4-aminophthalic acid
1-(4-aminophenyl)ethanol
4-aminobenzyl alcohol
4-amino-3-methoxybenzoic acid
4-aminophenyl ethyl carbinol
4-amino-3-nitrobenzoic acid
4-amino-3,5-dinitrobenzoic acid
4-amino-3,5-dichlorobenzoic acid
4-amino-3-hydroxybenzoic acid
4-aminobenzyl alcohol hydrochloride
4-aminobenzoic acid hydrochloride
pararosaniline base
4-amino-5-chloro-2-methoxybenzoic acid
4-(hexafluoro-2-hydroxyisopropyl)aniline
piperazine-p-amino benzoate
4-amino-3,5-dibromobenzoic acid
isonicotinic acid hydrazide p-aminosalicylate salt
4-amino-3,5-diiodosalicylic acid
4-amino-2-methoxybenzoic acid
2-[2-(4-aminophenyl)-2-hydroxy-1-(hydroxymethyl)ethyl]isoindoline-1,3-dione
4-amino-2-nitrobenzoic acid
2,4-diaminobenzoic acid
p-aminobenzoic acid,
[3,5-3h]-4-amino-2-methoxybenzoic acid
L-(+)-threo-2-amino-1-(4-aminophenyl)-1,3-propanediol
L-(+)-threo-2-(N,N-dimethylamino)-1-(4-aminophenyl)-1,3-propanediol
ethyl 2-(4-aminophenyl)-3,3,3-trifluoro-2-hydroxypropanoate
ethyl 2-(4-amino-3-methylphenyl)-3,3,3-trifluoro-2-hydroxypropanoate
ethyl 2-(4-amino-3-methoxyphenyl)-3,3,3-trifluoro-2-hydroxypropanoate
3,4-diaminobenzyl alcohol dihydrochloride
4-aminonaphthalene-1,8-dicarboxylic acid
4-amino-3-chloro-5-methylbenzoic acid
4-amino-2,6-dimethylbenzoic acid
4-amino-3-fluorobenzoic acid
4-amino-5-bromo-2-methoxybenzenecarboxylic acid
2,7-diaminofluorene
4,4'-diaminooctafluorobiphenyl
3,3'-diaminobenzidine
3,3',5,5'-tetramethylbenzidine
3,3'-dimethoxybenzidine
o-tolidine
3,3'-dinitrobenzidine
2-nitrobenzidine
3,3'-dihydroxybenzidine
o-tolidine sulfone
benzidine,
3,3'-dichlorobenzidine
2,2',5,5'-tetrachlorobenzidine,
benzidine-3,3'-dicarboxylic acid
4,4'-diamino-1,1'-binaphthyl
4,4'-diaminodiphenyl-3,3'-diglycolic acid
dihydroethidium
o-dianisidine
2,2'-dichloro-5,5'-dimethoxybenzidine
3-methoxybenzidine
3,3'-dichlorobenzidine (diphenyl-d6),
2,7-diamino-9-fluorenone
3,5,3',5'-tetrabromo-biphenyl-4,4'-diamine
2,2'-bis(trifluoromethyl)benzidine
2,2'-dichloro[1,1'-biphenyl]-4,4'-diamine
3,9-diamino-1,11-dimethyl-5,7-dihydro-dibenzo(a,c)cyclohepten-6-one
3,3'-bis(trifluoromethyl)benzidine
dibenzo(1,2)dithiine-3,8-diamine
3,3'-tolidine-5-sulfonic acid
3,3'-dichlorobenzidine-d6
tetramethylbenzidine
3,3'-diaminobenzophenone, 3,3'-diaminodiphenylmethane,
4,4-bis-(3-amino-4-hydroxyphenyl)-valeric acid
2,2-bis(3-amino-4-hydroxyphenyl)hexafluoropropane
2,2-bis(3-amino-4-methylphenyl)hexafluoropropane
tetrabromo methylenedianiline
2,7-diamino-9-fluorenone
2,2-bis(3-aminophenyl)hexafluoropropane
bis-(3-amino-4-chloro-phenyl)-methanone
bis-(3-amino-4-dimethylamino-phenyl)-methanone
3-[3-amino-5-(trifluoromethyl)benzyl]-5-(trifluoromethyl)aniline
1,5-diaminonaphthalene
or their derivatives, again with the proviso that compounds listed which do not carry two amino groups are taken as derivatives with at least one additional amino group.

Preferred examples of additional other diamines are:
ethylenediamine, 1,3-propylenediamine, 1,4-butylenediamine, 1,5-pentylenediamine,
1,6-hexylenediamine, 1,7-heptylenediamine, 1,8-octylenediamine,
1,9-nonylenediamine, 1,10-decylenediamine, 1,11-undecylenediamine,
1,12-dodecylenediamine, α,α'-diamino-m-xylene, α,α'-diamino-p-xylene,
(5-amino-2,2,4-trimethylcyclopentyl)methylamine, 1,2-diaminocyclohexane,
4,4'-diaminodicyclohexylmethane, 1,3-bis(methylamino)cyclohexane,
4,9-dioxadodecane-1,12-diamine, 3,5-diaminobenzoic acid methyl ester,
3,5-diaminobenzoic acid hexyl ester, 3,5-diaminobenzoic acid dodecyl ester,
3,5-diaminobenzoic acid isopropyl ester, 4,4'-methylenedianiline, 4,4'-ethylenedianiline,
4,4'-diamino-3,3'-dimethyldiphenylmethane, 3,3',5,5'-tetramethylbenzidine,
4,4'-diaminodiphenyl sulfone, 4,4'-diaminodiphenyl ether, 1,5-diaminonaphthalene,
3,3'-dimethyl-4,4'-diaminobiphenyl, 3,4'-diaminodiphenyl ether,
3,3'-diaminobenzophenone, 4,4'-diaminobenzophenone,
4,4'-diamino-2,2'-dimethylbibenzyl, bis[4-(4-aminophenoxy)phenyl]sulfone, 1,4-bis(4-aminophenoxy)benzene, 1,3-bis(4-aminophenoxy)benzene,
1,3-bis(3-aminophenoxy)benzene, 2,7-diaminofluorene,
9,9-bis(4-aminophenyl)fluorene, 4,4'-methylene-bis(2-chloroaniline),
4,4'-bis(4-aminophenoxy)biphenyl, 2,2',5,5'-tetrachloro-4,4'-diaminobiphenyl,
2,2'-dichloro-4,4'-diamino-5,5'-dimethoxybiphenyl, 3,3'-dimethoxy-4,4'-diaminobiphenyl,
4,4'-(1,4-phenyleneisopropylidene)bisaniline,
4,4'-(1,3-phenyleneisopropylidene)bisaniline,
2,2-bis[4-(4-aminophenoxy)phenyl]propane,
2,2-bis[3-(4-aminophenoxy)phenyl]hexafluoropropane,
2,2-bis[3-amino-4-methylphenyl]hexafluoropropane,
2,2-bis(4-aminophenyl)hexafluoropropane,
2,2'-bis[4-(4-amino-2-trifluoromethylphenoxy)phenyl] hexafluoropropane,
4,4'-diamino-2,2'-bis(trifluoromethyl)biphenyl, and
4,4'-bis[(4-amino-2-trifluoromethyl)phenoxy]-2,3,5,6,2',3',5',6'-octafluorobiphenyl.

The polymers of the present invention have a molecular weight $M_W$ between 1 000 and 5 000 000, preferably however between 5 000 and 2 000 000, especially advantageously however between 10 000 and 1 000 000.

The number of monomer building blocks from which the polymer chains according to the invention are synthesised can vary within a wide range. It is generally from 2 to 2000, but especially from 3 to 200.

The polymers according to the invention may further contain additives such as silane-containing compounds and epoxy-containing crosslinking agents for further improving the adhesion of the polymer to a substrate. Example for silane adhesion promoters were described in the literature, for example *Plast. Eng.* 36 (1996) (Polyimides, fundamentals and applications). The above epoxy-containing crosslinking agent preferably includes 4,4'-methylenebis(N,N-diglycidylaniline), trimethylolpropane triglycidyl ether, benzene-1,2,4,5-tetracarboxylic acid 1,2:4,5-N,N'-diglycidyldiimide, polyethylene glycol diglycidyl ether, N,N-diglycidylcyclohexylamine and the like.

The polymers according to the invention may contain additives such a photosensitiser, a photoradical generator and/or a cationic photoinitiator. Example for such additives were 2,2-dimethoxyphenylethanone, mixture of diphenylmethanone and N,N-dimethylbenzenamine or ethyl 4-(dimethylamino)benzoate, xanthone, thioxanthone, IRGACURE™ 184, 369, 500, 651 and 907 (Ciba), Michler's ketone, triaryl sulfonium salt and the like.

The polymers according to the invention may be used as a single polymer or as mixture with other polymers, oligomers, monomers, photoactive polymers, photoactive oligomers and/or photoactive monomers. Thus the properties of the layer may be modified to give what is sought. For example, an induced pretilt angles, good surface wetting, high voltage holding ratio, a specific anchoring energy etc. may be obtained.

The polymers according to the invention can then be applied to a support and, after any imidisation step which may be necessary, crosslinked by irradiation with aligning light, preferably with linearly polarised light, that is to say by cycloaddition of their side-chains containing the photoreactive group, there being obtained, depending upon the direction of polarisation of the light radiated in, a preferred direction of orientation and of the angle of tilt for liquid crystals that are bought into contact with the alignment layer. By spatially selective irradiation of the molecular units according to the invention it is hence possible for very specific regions of a surface to be aligned and provided with a defined angle of tilt. At the same time the alignment layer so produced is also stabilised by the cycloaddition.

Such alignment layers can be produced, for example, by first preparing a solution of the resulting polymer material, which is applied to a support, which is optionally coated with an electrode (for example a glass plate coated with indium-tin oxide (ITO)), in a spin-coating apparatus, so that homogeneous layers of 5 nanometer to 2 micrometer thickness are produced. Then, or optionally after prior imidisation, the regions to be oriented can be irradiated, for example, with a high-pressure mercury vapour lamp, a xenon lamp or a pulsed UV laser, using a polariser and optionally a mask for creating images of structures. The irradiation time is dependent upon the output of the individual lamps and can vary from a few seconds to several hours. The photoreaction can also be carried out, however, by irradiation of the homogeneous layer using filters that, for example, allow only the radiation suitable for the crosslinking reaction to pass through.

Such alignment layers of the invention may be used in the production of optical or electro-optical devices having at least one orientation layer as well as unstructured and structured optical elements and multi-layer systems. Thus the invention further relates to an optical or electro-optical device comprising one or more oligomers, dendrimers or polymers according to the present invention; preferably in cross-linked form.

The technical advantage of the novel compounds of the present invention is their high contrast, in several application for the orientation for polymerizable and movable liquid crystals, In addition, high speed of orientation can be accesses and good azimuthal stability. The latter property is important for the provion of structured retarders such a optical films for 3 D, security devices, functional foils such as barrier layers.

The examples which follow further illustrate the invention. They are given by way of illustration and not by way of limitation. Variations on these examples falling within the scope of the invention will be apparent to a person skilled in the art.

EXAMPLES

Definitions used in the examples:
LC/MS: Liquid chromatography/Mass spectrometry

[M+Na]=Molecular Mass plus sodium
[M+H]=Molecular Mass plus proton
[M+NH$_4$]=Molecular Mass plus ammonium
$^1$H NMR=$^1$H nuclear magnetic resonance spectroscopy
DMSO-d$_6$=dimethylsulfoxid deuterated
THF-d$_8$=Tetrahydrofuran deuterated
300 MHz=300 Megahertz
m=multiplet
d=douplet
dd=doublet doublet
t=triplet
s=singulet
q=quintet
br=broad
δ=chemical shift
HCl=hydrogen chloride
MeOH: methanol
EtOAc: ethyl acetate
NMP: N-methyl-2-pyrrolidone
THF: tetrahydrofuran
TBME: tert. butyl methyl ether
DMF: N,N-dimethylformamide
RT: room temperature, usually in the range of 18° C. to 28° C.
[η]: viscosity
v.t. %: volume percent
MLC7067: is a mixture of liquid crystal available from Merck KGA with a Dielectric anisotropy of 10.3, an optical anisotropy of 0.1025 and a rotational viscosity of 81 m·Pa·s.

Example 1

Preparation of {4-[(8-hydroxyoctyl)oxy]phenyl}acetonitrile 1A

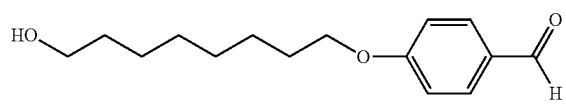 [SMILES: O=Cc1ccc(OCCCCCCCCO)cc1]

20.0 g (150 mmol) of (4-hydroxyphenyl)acetonitrile and 29.5 g (179 mmol) of 8-chlorooctan-1-ol are dissolved in 400 mL of N,N-dimethylformamide. 41.5 g (300 mmol) of potassium carbonate and 5.0 g (30 mmol) of potassium iodide are added and the suspension is heated to 80° C. After 48h, the excess of potassium carbonate is filtered off and the resulting filtrate is poured to icy water. The aqueous layer is extracted twice with ethyl acetate. Combined organic layers are washed with brine and evaporated to dryness. The crude is purified twice on SiO2 column chromatography with Heptane/ethyl acetate: 7/3 as eluant and dried overnight at 40° C. 24.5 g of {4-[(8-hydroxyoctyl)oxy]phenyl}acetonitrile are obtained as a yellow solid (62% yield).

The compounds 1B, 1C are prepared according to the process described in example 1 for compound 1A with the proviso that 8-chlorooctan-1-ol is replaced by 6-bromohexan-1-ol, respectively 11-bromoundecan-1-ol.

The compounds 1D is prepared according to the process described in example 1 for compound 1C with the proviso that (4-hydroxyphenyl)acetonitrile is replaced by [4-hydroxy-3-methoxy-phenyl]acetonitrile The compounds 1E is prepared according to the process described in example 1 for compound 1D with the proviso that 11-bromoundecan-1-ol is replaced by 8-chlorooctan-1-ol.

Example 2

Preparation of 4-[(8-hydroxyoctyl)oxy]benzaldehyde

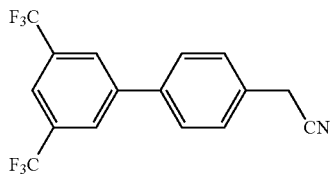

4-[(8-hydroxyoctyl)oxy]benzaldehyde is prepared starting from 4-hydroxybenzaldehyde and 8-chlorooctan-1-ol according to the procedure described example 1 in 62% yield.

Example 4

Preparation of [3',5'-bis(trifluoromethyl)-1,1'-biphenyl-4-yl]acetonitrile 0.664 g (3.4 mmol) of (4-bromophenyl)acetonitrile, 0.645 g (3.4 mmol) of [3,5-bis(trifluoromethyl)phenyl]boronic acid and 937 mg (6.8 mmol) of potassium carbonate are dissolved in 20 mL of tetrahydrofuran and 5 mL of water. The solution is purged with argon and 78 mg of tetrakis(triphenylphosphine)palladium(0) are added. The solution is purged with argon and heated to 80° C. After 12h at 80° C., the reaction mixture is cooled to room temperature, and the aqueous layer is extracted twice with ethyl acetate. Combined organic layers are washed with brine and evaporated to dryness. The crude is purified twice on SiO$_2$ column chromatography with Heptane/ethyl acetate 3/2 as eluant and dried overnight at 30° C. 527 mg of Example 4 are obtained as a white solid.

Example 6

Preparation of (2Z)-2-{4-[(8-hydroxyoctyl)oxy]phenyl}-3-[4-(trifluoromethyl)phenyl]prop-2-enenitrile 6A

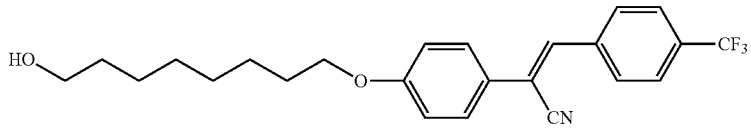 [SMILES: N#C/C(=C\c1ccc(C(F)(F)F)cc1)c1ccc(OCCCCCCCCO)cc1]

5.0 g (19.1 mmol) of Example 1A, 3.5 g (19.1 mmol) of 4-(trifluoromethyl)benzaldehyde are dissolved in 50 mL of propan-2-ol. The solution is heated to 60° C. and 1.9 mL (1.9 mmol) of a 1M solution of tetrabuthylamoniumhydroxyde in methanol are added dropwise. After 2h at 60° C., the reaction mixture is cooled down to 0° C. The precipitate is filtered off, washed with cold propan-2-ol and recristalized in propan-2-ol. 4.7 g of Example 6A are obtained as a white solid (59% yield).

The compounds 6B, 6E, 6H, 6 X, 6U, 6V, 6AA, 6AB is prepared according to the process described in example 6 for compound 6A with the proviso that 4-(trifluoromethyl)benzaldehyde is replaced by 3,5-(trifluoromethyl)benzaldehyde, respectively 3-(trifluoromethyl)benzaldehyde, respectively 4-fluorobenzaldehyde, respectively benzaldehyde, respectively 4-chlorobenzaldehyde, respectively 4-bromobenzaldehyde, respectively 3,4,5-trifluorobenzaldehyde, respectively 4,6-difluorobenzaldehyde.

The compounds 6 J, 6K, 6L is prepared according to the process described in example 6 for compound 6A with the proviso that Example 1A is replaced by Example 1E, respectively by Example 1B, respectively by Example 1D.

The compounds 6N is prepared according to the process described in example 6 for compound 6B with the proviso that Example 1A is replaced by Example 1C.

Example 7

Preparation of (2Z)-3-{4-[(8-hydroxyoctyl)oxy]phenyl}-2-[4-(trifluoromethyl)phenyl]prop-2-enenitrile 7A

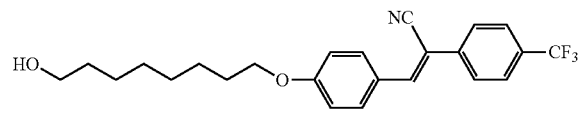

Example 7A is prepared starting from Example 2 and [(4-trifluoromethyl)phenyl]acetonitrile according to the procedure described in example 6 in 76% yield.

The compounds 7B, 7D, 7E, 7W, 7Y are prepared according to the process described in example 7 for compound 7A with the proviso that [(4-trifluoromethyl)phenyl]acetonitrile is replaced by {[(3,5-bis(trifluoromethyl)]phenyl}acetonitrile, respectively Example 4, respectively [(4-fluoro)phenyl]acetonitrile, respectively [(4-chloro)phenyl]acetonitrile, respectively [(4-bromo)phenyl]acetonitrile, respectively [(3,4,5-Trifluoro)phenyl]acetonitrile, respectively [(4,6-difluoro)phenyl]acetonitrile.

Example 10

Preparation of 8-(4-{(Z)-1-cyano-2-[4-(trifluoromethyl)phenyl]ethenyl}phenoxy)octyl 2-methylacrylate 10A

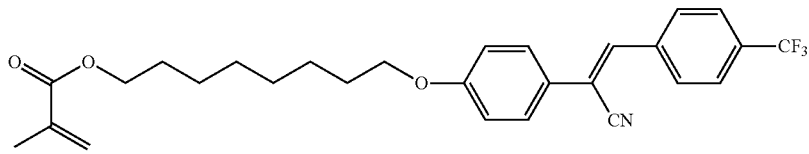 [SMILES: C=C(C)C(=O)OCCCCCCCCOc1ccc(/C(C#N)=C/c2ccc(C(F)(F)F)cc2)cc1]

2.03 g (4.9 mmol) of Example 6A, 59 mg (0.49 mmol) of 4-dimethylaminopyridine and 1.48 g (14.69 mmol) of triethylamine are dissolved in 40 mL of tetrahydrofurane. The solution is cooled down to 0° C. and a solution 0.9 g (5.8 mmol) of methacrylic anhydride in 10 mL of tetrahydrofuran is added dropwise in 1h at 0° C. After 2h at 0° C., the reaction mixture is then allowed to heat up to room temperature. After 15h, the reaction mixture is poured onto icy water. The precipitate is filtered off, dried at 30° C. and recristalized in methanol with a small amount of 2,6-di-tert-butyl-4-methylphenol. 1.4 g of Example 10A are obtained as a white solid (61% yield).

The compounds 10B, 10E, 10F, 10H, 10I, 10L, 10M, 10N, 10O, 10P, 10R, 10S, 10U, 10V, 10W, 10Y, 10AA, 10AB are prepared according to the process described in example 10 for compound 10A with the proviso that Example 6A is replaced by Example 6B, respectively, respectively Example 7A, respectively Example 7B, respectively Example 7D, respectively Example 6E, respectively Example 6J, respectively Example 6H, respectively Example 7E, respectively Example 6X, respectively Example 6K, respectively Example 6N, respectively Example 6L, respectively Example 6U, respectively Example 6V, respectively Example 7W, respectively Example 7Y, respectively 6AA, respectively 6AB.

Analytical data of compounds are given in the following table:

| | Structure | Analytical data |
|---|---|---|
| 10A | (methacrylate-O-(CH₂)₈-O-C₆H₄-C(CN)=CH-C₆H₄-CF₃) | LC/MS: [M + H]⁺ = 486.2 |
| 10B | (methacrylate-O-(CH₂)₈-O-C₆H₄-C(CN)=CH-C₆H₃(CF₃)₂) | LC/MS: [M + Na]⁺ = 576.7 |
| 10E | (methacrylate-O-(CH₂)₈-O-C₆H₄-CH=C(CN)-C₆H₄-CF₃) | LC/MS: [M + Na]⁺ = 508.2 |
| 10F | (methacrylate-O-(CH₂)₈-O-C₆H₄-CH=C(CN)-C₆H₃(CF₃)₂) | LC/MS: [M + Na]⁺ = 576.1 |
| 10H | (methacrylate-O-(CH₂)₈-O-C₆H₄-CH=C(CN)-C₆H₄-C₆H₃(CF₃)₂) | LC/MS: [M + NH₄]⁺ = 647.2 |
| 10I | (methacrylate-O-(CH₂)₈-O-C₆H₄-C(CN)=CH-C₆H₄-CF₃ (meta)) | LC/MS: [M + Na]⁺ = 508.2 |
| 10L | (methacrylate-O-(CH₂)₈-O-C₆H₃(OMe)-C(CN)=CH-C₆H₄-CF₃) | LC/MS: [M + Na]⁺ = 538.1 |

-continued
| | Structure | Analytical data |
|---|---|---|
| 10M | 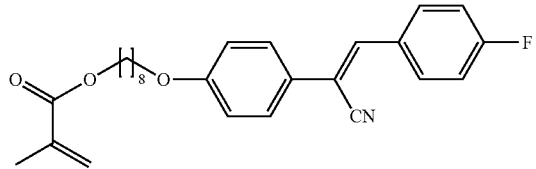 | LC/MS: [M + Na]+ = 458.1 |
| 10N | 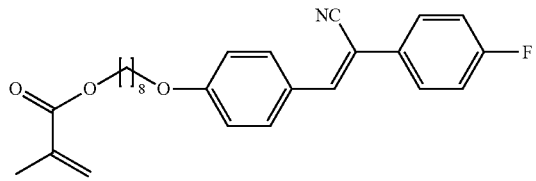 | LC/MS: [M + H]+ = 436.2 |
| 10O | 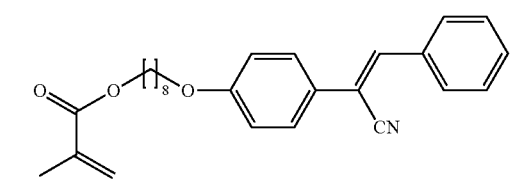 | LC/MS: [M + Na]+ = 440.5 |
| 10P | 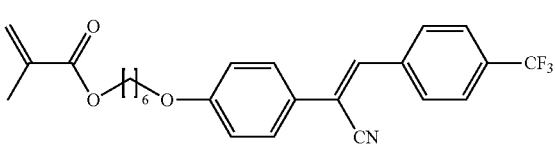 | LC/MS: [M + Na]+ = 480.1 |
| 10R | 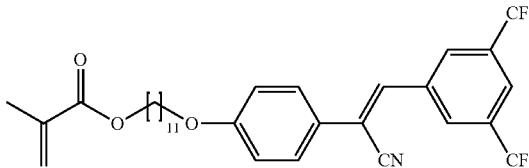 | LC/MS: [M + Na]+ = 618.1 |
| 10S | 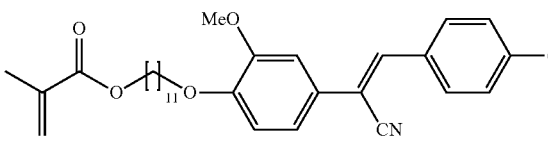 | LC/MS: [M + Na]+ = 580.2 |
| 10U | 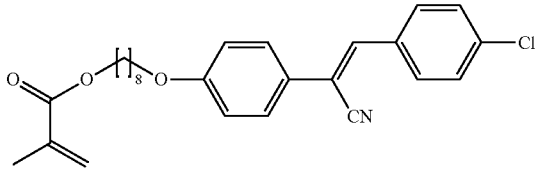 | LC/MS: [M + Na]+ = 474.1 |
| 10V | 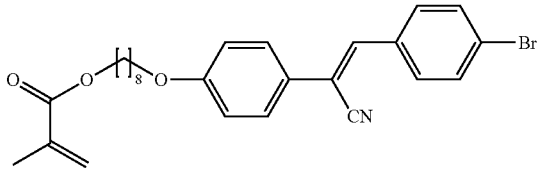 | LC/MS: [M + Na]+ = 518.1 |
| 10W | 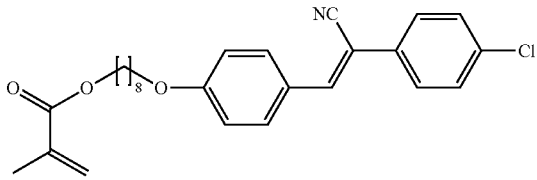 | LC/MS: [M + Na]+ = 474.1 |

| | Structure | Analytical data |
|---|---|---|
| 10Y | 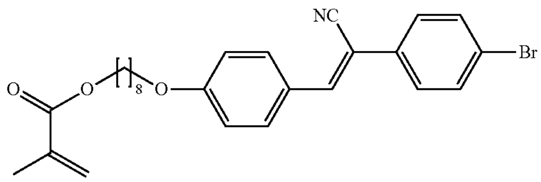 | LC/MS: [M + Na]$^+$ = 518.1 |
| 10AA | 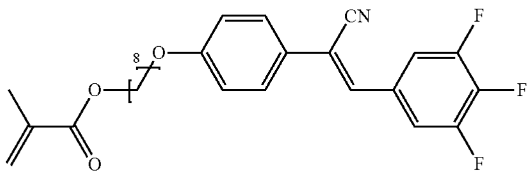 | $^1$H NMR DMSO-d$_6$ (300 MHz): 7.89 (s, 1H), 7.81 (m, 2H), 7.67 (d, 2H), 7.08 (d, 2H), 6.01 (s, 1H), 5.66 (s, 1H), 4.09 (dd, 2H), 4.02 (dd, 2H), 1.87 (s, 3H), 1.73 (m, 2H), 1.62 (m, 2H), 1.33 (m, 8H). |
| 10AB | 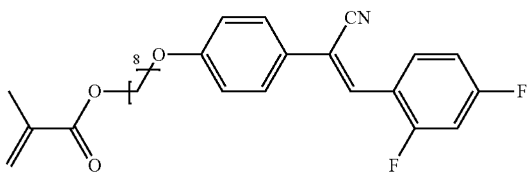 | $^1$H NMR DMSO-d$_6$ (300 MHz): 8.04 (dd, 1H), 7.82 (s, 1H), 7.69 (dd, 2H), 7.45 (dd, 1H), 7.29 (dd, 1H), 7.06 (d, 2H), 6.01 (s, 1H), 5.66 (s, 1H), 4.09 (m, 2H), 4.02 (m, 2H), 1.87 (s, 3H), 1.72 (m, 2H), 1.61 (m, 2H), 1.33 (m, 8H). |

Example 11

Preparation of 8-(4-{(Z)-1-cyano-2-[4-(trifluoromethyl)phenyl]ethenyl}phenoxy)octyl poly-2-methylacrylate 11A 2.00 g (4.1 mmol) of Example 10A are dissolved in 10 mL of degassed cyclohexanone. The solution is purged with argon and heated to 60° C. A solution of 20.0 mg (0.14 mmol) of 2,2'-Azobis(2-methylpropionitrile) in 2 mL of cyclohexanone is added dropwise. After 36h at 60° C., the reaction mixture is cooled down to room temperature, diluted with 5 mL of tetrahydrofuran, and precipitated in 200 mL of cold methanol. The precipitate is filtered off, washed with methanol and dried overnight at 30° C. 1.50 g of Example 11A are obtained as a white solid (75% yield).

The compounds 11B, 11E, 11F, 11H, 11I, 11L, 11M, 11N, 11O, 11P, 11R, 11S, 11U, 11V, 11W, 11Y, 11AA, 11AB are prepared according to the process described in example 11 for compound 11A with the proviso that Example 10A is replaced by Example 10B, respectively Example 10E, respectively Example 10F, respectively Example 10H, respectively Example 10I, respectively Example 10L, respectively Example 10M, respectively Example 10N, respectively Example 10O, respectively Example 10P, respectively Example 10R, respectively Example 10S, respectively Example 10U, respectively Example 10V, respectively Example 10W, respectively Example 10Y, respectively Example 10AA, respectively Example 10AB.

| | Name | $^1$H NMR (300 MHz) in THF-d$_8$ | Mw GPC-PS-equivalent |
|---|---|---|---|
| 11A | 8-(4-{(Z)-1-cyano-2-[4-(trifluoromethyl)phenyl]ethenyl}phenoxy)octyl poly-2-methylacrylate | 7.98 (d, 2H), 7.70 (d, 2H), 7.64 (m, 3H), 6.94 (d, 2H), 3.96 (m, 4H), 3.82 (s, 3H), 1.84-1.61 (m, 2H), 1.64 (m, 2H), 1.56-1.20 (m, 10H), 1.15-0.79 (m, 3H) | 166 000 |
| 11B | 8-(4-{(Z)-2-[3,5-bis(trifluoromethyl)phenyl]-1-cyanoethenyl}phenoxy)octyl poly-2-methylacrylate | 8.43 (s, 2H), 8.04 (s, 1H), 7.78 (s, 1H), 7.67 (d, 2H), 6.97 (d, 2H), 4.00 (m, 4H), 3.82 (s, 3H), 1.84-1.61 (m, 2H), 1.64 (m, 2H), 1.56-1.20 (m, 10H), 1.15-0.79 (m, 3H) | 101 900 |
| 11E | 8-(4-{(Z)-2-cyano-2-[4-(trifluoromethyl)phenyl]ethenyl}phenoxy)octyl poly-2-methylacrylate | 7.92 (d, 2H), 7.81 (d, 2H), 7.74 (s, 1H), 7.68 (d, 2H), 6.96 (d, 2H), 3.98 (m, 4H), 3.82 (s, 3H), 1.84-1.61 (m, 2H), 1.64 (m, 2H), 1.56-1.20 (m, 10H), 1.15-0.79 (m, 3H) | 79 000 |
| 11F | 8-(4-{(Z)-2-[3,5-bis(trifluoromethyl)phenyl]-2-cyanoethenyl}phenoxy)octyl poly-2-methylacrylate | 8.19 (m, 2H), 7.97 (m, 2H), 7.93 (m, 2H), 6.98 (dd, 2H), 4.00 (m, 4H), 3.82 (s, 3H), 1.84-1.61 (m, 2H), 1.64 (m, 2H), 1.56-1.20 (m, 10H), 1.15-0.79 (m, 3H) | 66 300 |

-continued

| | Name | $^1$H NMR (300 MHz) in THF-$d_8$ | Mw GPC-PS-equivalent |
|---|---|---|---|
| 11H | 8-(4-{(Z)-2-[3',5'-bis(trifluoromethyl)-1,1'-biphenyl-4-yl]-2-cyanoethenyl}phenoxy)octyl poly-2-methylacrylate | 8.17 (m, 2H), 7.92 (m, 3H), 7.77 (m, 5H), 6.94 (d, 2H), 3.97 (m, 4H), 3.82 (s, 3H), 1.84-1.61 (m, 2H), 1.64 (m, 2H), 1.56-1.20 (m, 16H), 1.15-0.79 (m, 3H) | 66 000 |
| 11I | 8-(4-{(Z)-1-cyano-2-[3-(trifluoromethyl)phenyl]ethenyl} phenoxy)octyl poly-2-methylacrylate | 8.15 (d, 2H), 8.09 (s, 1H), 7.80-7.50 (m, 5H), 6.94 (d, 2H), 3.96 (m, 4H), 1.86-1.55 (m, 4H), 1.55-1.25 (m, 10H), 1.20-0.80 (m, 3H) | 62 000 |
| 11L | of 8-(4-{(Z)-1-cyano-2-[4-(trifluoromethyl)phenyl]ethenyl}-2-methoxyphenoxy)octyl poly-2-methylacrylate | 7.98 (d, 2H), 7.70 (d, 2H), 7.66 (s, 1H), 7.23 (m, 2H), 6.90 (d, 1H), 3.96 (m, 4H), 3.83 (s, 3H), 1.90-1.55 (m, 4H), 1.55-1.25 (m, 10H), 1.25-0.80 (m, 3H) | 24 200 |
| 11M | 8-{4-[(Z)-1-cyano-2-(4-fluorophenyl)ethenyl]phenoxy} octyl poly-2-methylacrylate | 7.91 (d, 2H), 7.59 (d, 2H), 7.54 (s, 1H), 7.15 (m, 2H), 6.92 (d, 2H), 3.94 (m, 4H), 1.90-1.55 (m, 4H), 1.55-1.25 (m, 10H), 1.25-0.80 (m, 3H) | 89 000 |
| 11N | 8-(4-{(Z)-2-cyano-2-[4-(fluoro)phenyl]ethenyl}phenoxy) octyl poly-2-methylacrylate | 7.86 (d, 2H), 7.66 (dd, 2H), 7.54 (s, 1H), 7.12 (dd, 2H), 6.94 (d, 2H), 3.97 (m, 4H), 1.90-1.55 (m, 4H), 1.55-1.25 (m, 10H), 1.25-0.80 (m, 3H) | 121 000 |
| 11O | 8-{4-[(Z)-1-cyano-2-phenylethenyl]phenoxy}octyl poly-2-methylacrylate | 7.86 (d, 2H), 7.51 (d, 2H), 7.56 (s, 1 H), 7.38 (m, 3H), 6.93 (d, 2H), 3.94 (m, 4H), 1.90-1.55 (m, 4H), 1.55-1.25 (m, 10H), 1.25-0.80 (m, 3H) | 349 000 |
| 11P | 6-(4-{(Z)-1-cyano-2-[4-(trifluoromethyl)phenyl]ethenyl} phenoxy)hexyl poly-2-methylacrylate | 7.97 (d, 2H), 7.69 (d, 2H), 7.63 (m, 1 + 2H), 6.93 (d, 2H), 3.96 (m, 4H), 1.90-1.55 (m, 4H), 1.55-1.25 (m, 6H), 1.25-0.80 (m, 3H) | 66 000 |
| 11R | 11-(4-{(Z)-2-[3,5-bis(trifluoromethyl)phenyl]-1-cyanoethenyl}phenoxy)undecyl poly-2-methylacrylate | 8.43 (s, 2H), 8.04 (s, 1H), 7.78 (s, 1H), 7.67 (d, 2H), 6.97 (d, 2H), 3.99 (m, 4H), 2.00-1.55 (m, 4H), 1.55-1.25 (m, 16H), 1.25-0.80 (m, 3H) | 111 700 |
| 11S | 11-(4-{(Z)-1-cyano-2-[4-(trifluoromethyl)phenyl]ethenyl}-poly-2-methoxyphenoxy)undecyl poly-2-methylacrylate | 7.99 (d, 2H), 7.73 (s, 1H), 7.69 (d, 2H), 7.26 (m, 2H), 6.91 (d, 1H), 3.96 (m, 4H), 3.83 (s, 3H), 2.00-1.55 (m, 4H), 1.55-1.25 (m, 16H), 1.25-0.80 (m, 3H) | 63 700 |
| 11U | 8-(4-{(Z)-1-cyano-2-[4-(chloro)phenyl]ethenyl}phenoxy) octyl poly-2-methylacrylate | 7.90 (d, 2H), 7.65 (m, 3H), 7.45 (d, 2H), 7.05 (m, 2H), 4.01 (m, 4H), 1.90-1.55 (m, 5H), 1.55-1.30 (m, 9H), 1.25-0.80 (m, 3H) | 58700 |
| 11V | 8-(4-{(Z)-1-cyano-2-[4-(bromo)phenyl]ethenyl}phenoxy) octyl poly-2-methylacrylate | 7.95 (d, 2H), 7.65 (m, 5H), 6.95 (d, 2H), 3.94 (m, 4H), 1.90-1.55 (m, 5H), 1.55-1.25 (m, 9H), 1.25-0.80 (m, 3H) | 62200 |
| 11W | 8-(4-{(Z)-2-cyano-2-[4-(chloro)phenyl]ethenyl}phenoxy) octyl poly-2-methylacrylate | 7.95 (d, 2H), 7.66 (m, 3H), 7.44 (d, 2H), 7.05 (d, 2H), 4.05 (m, 4H), 1.90-1.55 (m, 5H), 1.55-1.25 (m, 9H), 1.25-0.80 (m, 3H) | 64600 |
| 11Y | 8-(4-{(Z)-2-cyano-2-[4-(bromo)phenyl]ethenyl}phenoxy) octyl poly-2-methylacrylate | 7.95 (d, 2H), 7.66 (m, 5H), 7.05 (m, 2H), 4.05 (m, 4H), 1.90-1.55 (m, 5H), 1.55-1.25 (m, 9H), 1.25-0.80 (m, 3H) | 44800 |
| 11AA | 8-(4-{(Z)-1-cyano-2-[3, 4, 5-(trifluoro)phenyl]ethenyl}phenoxy)octyl poly-2-methylacrylate | 7.49 (m, 4H), 7.20 (s, 1H), 6.87 (m, 2H), 3.93 (m, 4H), 2.10-1.20 (m, 12H), 1.20-0.70 (m, 3H)* | 58000 |
| 11AB | 8-(4-{(Z)-1-cyano-2-[4-(4, 6 difluoro)phenyl]ethenyl}phenoxy octyl poly-2-methylacrylate | 20 (dd, 1H), 7.53 (d, 1H), 7.48 (s, 1H), 6.89 (m, 4H), 3.93 (m, 4H), 2.10-1.20 (m, 12H), 1.20-0.70 (m, 3H)* | 53000 |

*NMR made in CDCl$_3$

Example 12

Preparation of 6-{4-[(1E)-3-methoxy-3-oxoprop-1-enyl]phenoxy}hexyl poly-2-methylacrylate-Co-8-{4-[(Z)-1-cyano-2-phenylethenyl]phenoxy}octyl poly-2-methylacrylate (98:2 Ratio)

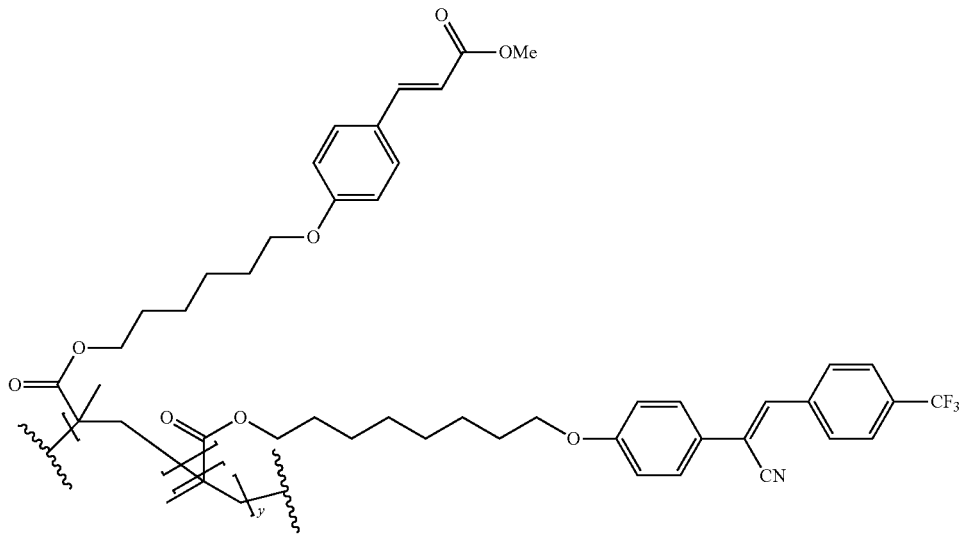

990 mg (2.858 mmol) of 6-{4-[(1E)-3-methoxy-3-oxoprop-1-enyl]phenoxy}hexyl 2-methylacrylate (example 4 of U.S. Pat. No. 6,107,427) and 28.6 mg (0.059 mmol) of Example 10A are dissolved in 5.0 mL of degassed cyclohexanone. The solution is purged with argon and heated to 60° C. A solution of 9.0 mg (0.055 mmol) of 2,2'-Azobis(2-methylpropionitrile) in 1 mL of cyclohexanone is added dropwise. After 17h at 60° C., the reaction mixture is cooled down to room temperature, diluted with 5 mL of tetrahydrofuran, and precipitated in 150 mL of cold methanol. The precipitate is filtered off, washed with methanol and dried overnight at 30° C. 864 mg of Example 12 are obtained as a white solid (85% yield). Size-exclusion chromatography (PS-equivalent): Mw 62,700.

Example 13

Preparation of 6-{4-[(1E)-3-methoxy-3-oxoprop-1-enyl]phenoxy}hexyl poly-2-methylacrylate-Co-8-{4-[(Z)-1-cyano-2-phenylethenyl]phenoxy}octyl poly-2-methylacrylate (95:5 Ratio)

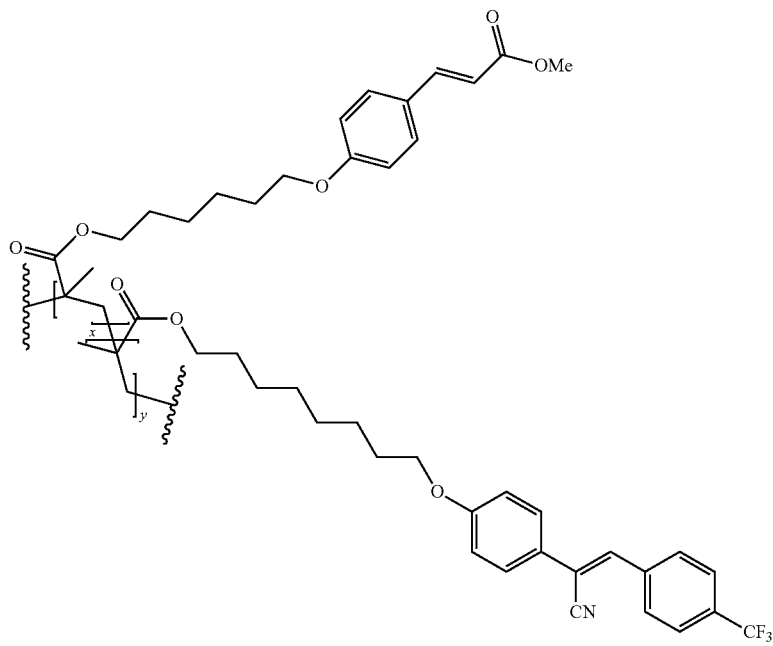

Example 13 is prepared starting 987 mg (2.849 mmol) of 6-{4-[(1E)-3-methoxy-3-oxoprop-1-enyl]phenoxy}hexyl 2-methylacrylate (example 4 of U.S. Pat. No. 6,107,427) and 73.8 mg (0.152 mmol) of Example 10A according to the procedure described for Example 12.

Size-exclusion chromatography (PS-equivalent): Mw 60,800.

Example 14

Preparation of 6-{4-[(1E)-3-methoxy-3-oxoprop-1-enyl]phenoxy}hexyl poly-2-methylacrylate-Co-8-{4-[(Z)-1-cyano-2-phenylethenyl]phenoxy}octyl poly-2-methylacrylate (90:10 Ratio)

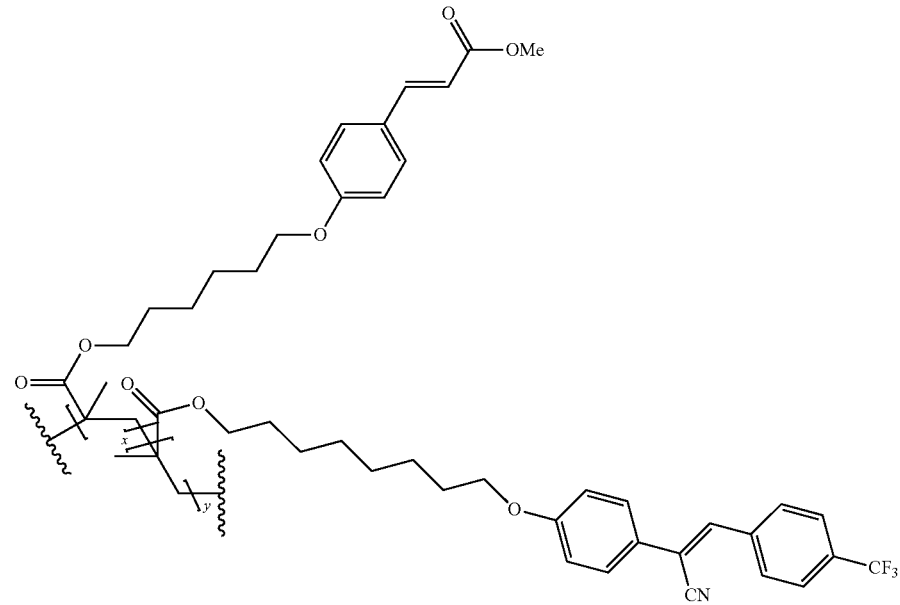

Example 14 is prepared starting 1000 mg (2.887 mmol) of example 4 of U.S. Pat. No. 6,107,427 and 156 mg (0.321 mmol) of Example 10A according to the procedure described for Example 12.

Size-exclusion chromatography (PS-equivalent), Mw 53,100.

Example 15

Preparation of 6-{4-[(1E)-3-methoxy-3-oxoprop-1-enyl]phenoxy}hexyl poly-2-methylacrylate-Co-8-{4-[(Z)-1-cyano-2-phenylethenyl]phenoxy}octyl poly-2-methylacrylate (90:10 Ratio)

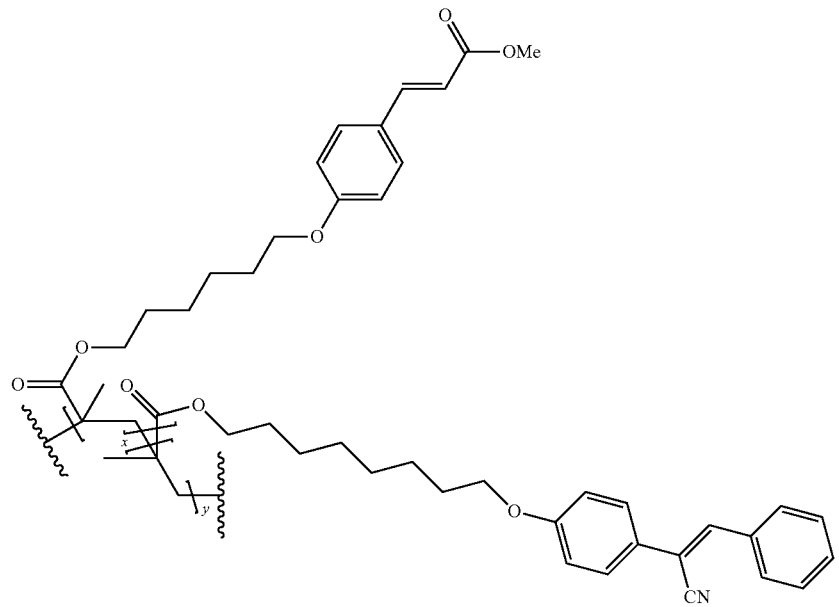

Example 15 is prepared starting 1000 mg (2.887 mmol) of example 4 of U.S. Pat. No. 6,107,427 and 134 mg (0.321 mmol) of Example 100 according to the procedure described for Example 12.

Size-exclusion chromatography (PS-equivalent) Mw 75,400.

Example 16

Preparation of 6-{4-[(1E)-3-methoxy-3-oxoprop-1-enyl]phenoxy}hexyl poly-2-methylacrylate-Co-8-{4-[(Z)-1-cyano-2-(4-fluorophenyl)ethenyl]phenoxy}octyl poly-2-methylacrylate (90:10 Ratio)

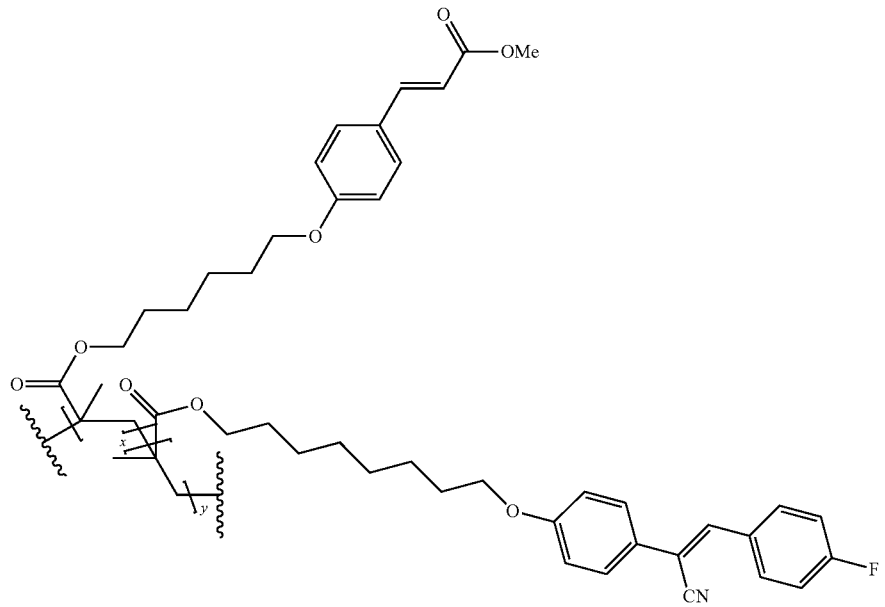

Example 16 is prepared starting 1000 mg (2.887 mmol) of Example 4 of U.S. Pat. No. 6,107,427 and 140 mg (0.321 mmol) of Example 10M according to the procedure described for Example 12.

Size-exclusion chromatography (PS-equivalent) Mw 78,900.

Example 17

Preparation of 4-[(11-hydroxyundecyl)oxy]benzaldehyde 17A

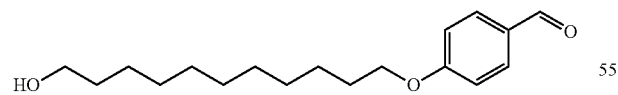

Example 17A is prepared starting from 4-hydroxybenzaldehyde and 11-bromoundecan-1-ol according to the procedure described for Example 2 in 57% yield. Example 17B is prepared starting from 4-hydroxy-3-methoxybenzaldehyde and 11-bromoundecan-1-ol according to the procedure described for Example 2 in 97% yield.

Example 18

Preparation of (Z)-2-(4-fluorophenyl)-3-[4-(11-hydroxyundecoxy)phenyl]prop-2-enenitrile

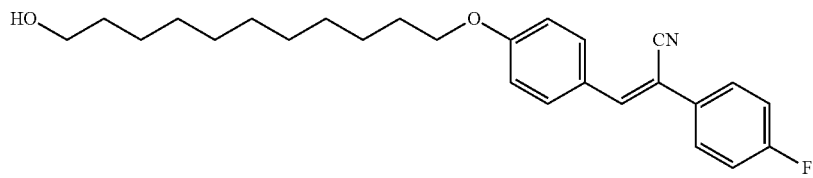 [SMILES: N#C/C(=C\c1ccc(OCCCCCCCCCCCO)cc1)c1ccc(F)cc1]

Example 18A is prepared starting from Example 17A and [(4-fluoro)phenyl]acetonitrile according to the procedure described in Example 7.

Example 20

(Z)-2-(4-fluorophenyl)-3-[4-(11-hydroxyundecoxy)phenyl]prop-1-enenitrile

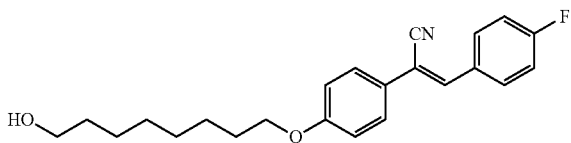 [SMILES: N#C/C(=C\c1ccc(F)cc1)c1ccc(OCCCCCCCCO)cc1]

Example 20 is prepared starting from Example 1A and 4-Fluorobenzaldehyde according to the procedure described in Example 7.

Example 21

Preparation of (Z)-2-(4-fluorophenyl)-3-[4-(11-hydroxyundecoxy)-3-methoxy-phenyl]prop-2-enenitrile

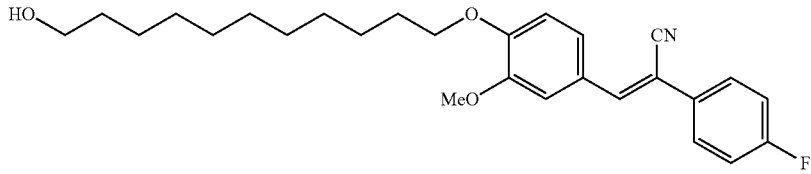 [SMILES: COc1cc(/C=C(\C#N)c2ccc(F)cc2)ccc1OCCCCCCCCCCCO]

Example 21 is prepared starting from Example 17B and [(4-fluoro)phenyl]acetonitrile according to the procedure described in Example 6.

Example 22

Preparation of 8-[4-[(Z)-2-cyano-2-(4-fluorophenyl)vinyl]phenoxy]octyl 3,5-dinitrobenzoate 22A

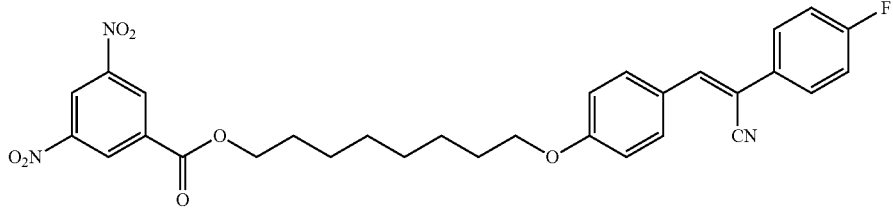 [SMILES: N#C/C(=C\c1ccc(OCCCCCCCCOC(=O)c2cc([N+](=O)[O-])cc([N+](=O)[O-])c2)cc1)c1ccc(F)cc1]

3290 mg (14.2 mmol) of 3,5-dinitrobenzoyl chloride is dissolved in 30 mL of toluene and 2 drops DMF. A solution of 5000 mg (13.6 mmol) of Example 19B, 160 mg (1.3 mmol) of 4-dimethylaminopyridine and 3240 mg (41.0 mmol) of pyridine in 10 mL of toluene are added slowly. The mixture is stirred at room temperature for 96 hours. The solution is then heated up to 80° C. and 10 ml of MeOH are added. The suspension is stirred at room temperature for 1 hour and at 0° C. for 1 hour. The precipitate is filtered off. The solid is dispersed in a mixture of 40 mL of MeOH and 10 mL of HCl 1N and is stirred 1h at room temperature. The suspension is filtered off, washed several time with cold MeOH and dried under high vacuum 12h to give 9600 mg (71%) of Example 22A.

Example 22B is prepared starting from Example 20 according to the procedure described in Example 22A.

Example 22C is prepared starting from Example 18A according to the procedure described in Example 22A Example 22F is prepared starting from Example 21 according to the procedure described in Example 22A.

Example 23

Preparation of 8-[4-[(Z)-2-cyano-2-(4-fluorophenyl)vinyl]phenoxy]octyl 3,5-diaminobenzoate 23A 4.8 g (5.55 mmol) of Example 22A are dissolved in a mixture of 63 ml of DMF and 7 ml of water. 13.8 g (51.3 mmol) of ferric chloride hexahydrate are added. 5.58 g (85.5 mmol) of zinc powder are added portionwise within 30 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Filtration of the residue on silica gel using toluene:ethyl acetate (1:3) as eluant and yields 3.56 g (99%) of Example 23A as a white powder.

The compounds 23B, 23C, 23F are prepared according to the process described in example 23 for compound 23A with the proviso that Example 22A is replaced by Example 22B, respectively Example 22C, respectively Example 22F.

| Name | | Structure | ¹H NMR (300 MHz) in DMSO-d6 |
|---|---|---|---|
| 23A | 8-[4-[(Z)-2-cyano-2-(4-fluorophenyl)vinyl]phenoxy]octyl 3,5-diamino-benzoate | 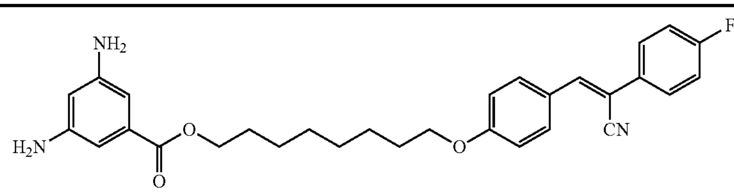 | 7.92 (d, 2H), 7.91 (s, 1H), 7.80-7.73 (m, 2H), 7.35 (dd, 2H), 7.09 (d, 2H), 6.43 (d, 2H), 6.02 (dd, 1H), 4.98 (s broad, 4H), 4.16 (t, 2H), 4.05 (t, 2H), 1.74 (m, 2H), 1.66 (m, 2H), 1.36 (m, 8H) |
| 23B | 8-[4-[(Z)-1-cyano-2-(4-fluorophenyl)vinyl]phenoxy]octyl 3,5-diamino-benzoate | 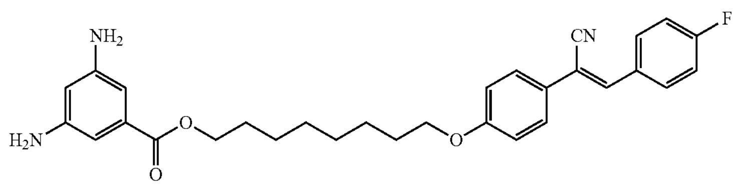 [SMILES: N#C/C(=C\c1ccc(F)cc1)c1ccc(OCCCCCCCCOC(=O)c2cc(N)cc(N)c2)cc1] | 7.96 (m, 2H), 7.91 (s, 1H), 7.65 (d, 2H), 7.38 (dd, 2H), 7.04 (d, 2H), 6.43 (d, 2H), 6.03 (dd, 1H), 4.99 (s, 4H), 4.16 (t, 2H), 4.02 (t, 2H), 1.70 (m, 4H), 1.36 (m, 8H) |
| 23C | 11-[4-[(Z)-2-cyano-2-(4-fluorophenyl)vinyl]phenoxy]undecyl 3,5-diamino-benzoate | 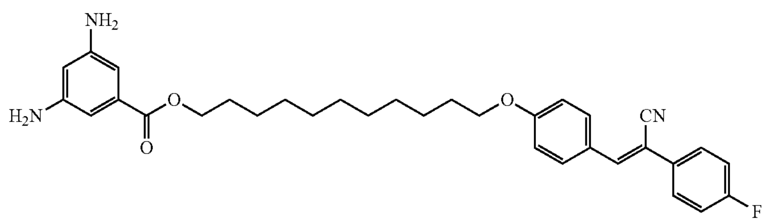 [SMILES: N#C/C(=C\c1ccc(OCCCCCCCCCCCOC(=O)c2cc(N)cc(N)c2)cc1)c1ccc(F)cc1] | 7.92 (d, 2H), 7.91 (s, 1H), 7.80-7.73 (m, 2H), 7.35 (dd, 2H), 7.09 (d, 2H), 6.43 (d, 2H), 6.02 (dd, 1H), 4.99 (s broad, 4H), 4.16 (t, 2H), 4.05 (t, 2H), 1.74 (m, 2H), 1.66 (m, 2H), 1.36 (m, 14H) |
| 23F | 11-[4-[(Z)-2-cyano-2-(4-fluorophenyl)vinyl]-2-methoxyphenoxy]undecyl 3,5-diamino-benzoate | 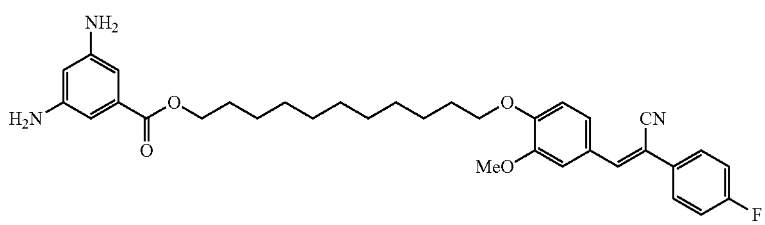 [SMILES: COc1cc(/C=C(\C#N)c2ccc(F)cc2)ccc1OCCCCCCCCCCCOC(=O)c1cc(N)cc(N)c1] | 7.91 (s, 1H), 7.79 (m, 2H), 7.66 (d, 1H), 7.55 (dd, 1H), 7.38 (m, 2H), 7.13 (d, 1H), 6.42 (d, 2H), 6.02 (t, 1H), 4.98 (s, 4H), 4.14 (t, 2H), 4.03 (t, 2H), 3.81 (s, 3H), 1.73 (m, 2H), 1.64 (m, 2H), 1.29 (m, 14H). |

Example 24

Preparation of PAA1

469 mg (2.4 mmol) of 1,2,3,4-cyclobutanetetracarboxylic acid is added to a solution of 1200 mg (2.4 mmol) of Example 23A in 6.6 g of NMP. Stirring is then carried out at 0° C. for 2 hours. The mixture is subsequently allowed to react for 21 hours at room temperature. The polymer mixture is diluted with 4.4 mL of NMP and precipitated into 150 mL of water to yield, after drying at 40° C. under vacuum, 1700 .mg of PAA-1 in the form of a white powder. η=0.38 dL/g

Example 25

Preparation of PAA-2 to PAA-7

In analogy to the preparation of PAA-1 (Example 24), PAA-2 to PAA-7 are prepared from diamine (see below table) with 2,3,5-tricarboxycyclopentylacetic-1,2:3,4-dianhydride. Analytical data are given in below table.

| Diamines | Polyamic acid | Viscosity (dL/g) |
|---|---|---|
| Example 23A | PAA-4 | 0.52 |
| Example 23B | PAA-2 | 0.38 |
| Example 23C | PAA-3 | 0.37 |
| Example 23F | PAA-7 | 0.42 |

Example 26

Preparation of Liquid Crystal Photo-polymerisable Monomer Formulation S2

A solution of 29.1 wt % LCM1, 0.3 wt % photoinitiator IRGACURE™ 369 from Ciba SC, 0.3 wt % of Tinuvine 123, and 0.3 wt % of BHT, is prepared using anisole as solvent. The solution is stirred for 30 minutes at room temperature and filtered on 0.20 μm PTFE hi-cap.

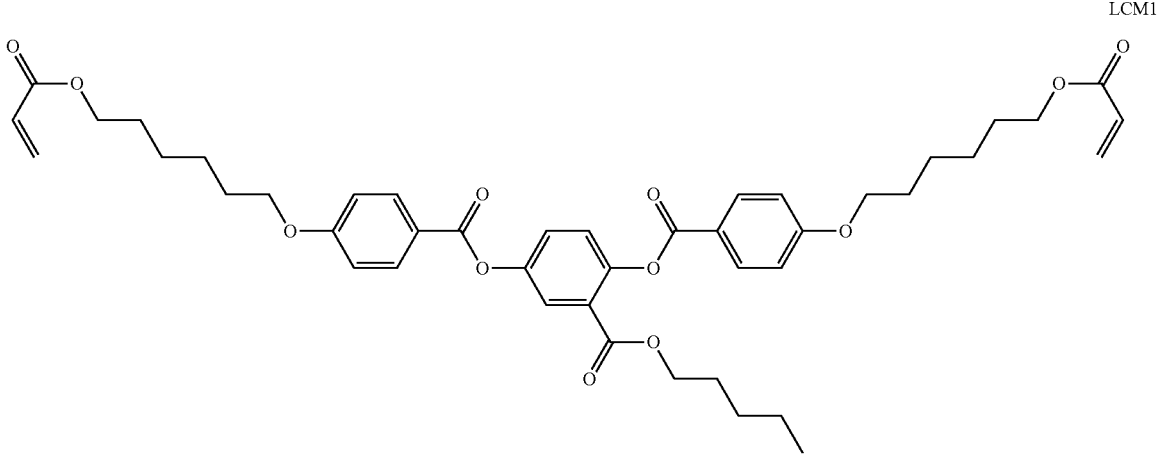 [SMILES: C=CC(=O)OCCCCCCOc1ccc(C(=O)Oc2ccc(OC(=O)c3ccc(OCCCCCCOC(=O)C=C)cc3)c(C(=O)OCCCCC)c2)cc1]

LCM1

Example 27

Application as Photoalignment Material

A two percent by weight solution S1 of material of the photoreactive polymer is prepared in cyclopentanone. The solution is stirred for 30 minutes at room temperature and filtered on 0.20 μm PTFE hi-cap. The solution is spin-coated at 2000 rpm onto a glass substrate, which is then dried for 5 minutes at 180° C. The substrate is subsequently irradiated with polarized UVA light from a mercury high-pressure lamp, the direction of incidence being perpendicular to the substrate surface. For the polarization a Moxtec polarizer is used. The exposure energy of the polarised UVA, using a Moxtec polariser, varied from 0.2 to 250 mJ·cm$^{-2}$. The formulation S2 (Example 26) is spin-coated at 800 rpm onto the substrate exposed with linearly polarised light, which is then dried for 30 seconds at 50° C. The resulting substrate is subsequently purged with nitrogen atmosphere for 30 seconds and then exposed with 1 J·cm$^{-2}$ of isotropic UV light under nitrogen atmosphere. The devices prepared are placed under Leitz microscope with crossed polarizers and the light intensity is measured separately in clear and dark state by a photomultiplier connected with the microscope and sending the results to a digital voltmeter. Contrast ratios are calculated from a following equation:

Contrast=$[I_{45}-I_{offset}]/[I_{0°}-I_{offset}]$, where:

$I_{0°}$ (V) is the minimal light intensity, i.e. the dark state
$I_{45°}$ (V) is the maximal light intensity, i.e. the clear state
$I_{offset}$ (V) is the light intensity measured without coating of S2 solution The minimum energy needed to obtain a good alignment (contrast>800) is determined for each compound. Contrasts at this specific energy are measured. The following table resumes the results obtained for photoreactive polymers from Examples 11A, Examples 11B, Examples 11F, Examples 11M, Examples 11N, Examples 11O, Examples 11P, Examples 11U, Examples 11V, Examples 11W, Examples 11Y, Examples 11I, Examples 11S.

| From examples | E min for orientation (mJ · cm2) | Contrast with Emin. |
|---|---|---|
| 11O | 1.6 | 1800 |
| 11N | 1.6 | 2600 |

-continued

| From examples | E min for orientation (mJ · cm2) | Contrast with Emin. |
|---|---|---|
| 11U | <0.6 | 4310 |
| 11V | <0.6 | 1190 |
| 11W | 1 | 3400 |
| 11Y | 1 | 900 |
| 11F | 12 | 1100 |
| 11B | 8 | 2220 |
| 11A | 1.3 | 3200 |
| 11R | 8 | 2300 |
| 11I | 4 | 1200 |
| 11M | 0.6 | 1600 |
| 11S | 8 | 1400 |
| 11P | 1.6 | 1300 |
| 11AA | 1 | 1480 |
| 11AB | 1.6 | 1470 |

Example 28

The high contrasts of devices prepared in Example 27 from Examples 11O, Examples 11N, Examples 11F, Examples 11E, Examples 11M are measured for an exposure energy of the polarised UVA of 150 mJ·cm.$^{-2}$ and presented in the following table.

| From examples | Contrast |
|---|---|
| 11O | 5500 |
| 11N | 8600 |
| 11F | 7800 |
| 11E | 6000 |
| 11M | 5000 |

Example 29

The azimuthal angle stability illustrates the stability of the first exposure E1 applied on photoalignment material with linearly polarized UV light and subsequently exposed with E2=E1 of this same light after the rotation of the sample at 45° according to the first irradiation direction. The method of double exposure at 0 and 45° defines the stability of LPP orientation through applied energy to be deviated if supplemental exposure is done at another planar angle. A two percent by weight solution made from photoreactive polymers formulation is prepared using cyclopentanone as solvent. The solution is stirred for 30 minutes at room temperature and filtered on 0.20 μm PTFE hi-cap. The solution is spin-coated at 2000 rpm onto a glass substrate, which is then dried for 5 minutes at 180° C. The substrate is subsequently irradiated with polarized UVA light from a mercury high-pressure lamp, the direction of incidence being perpendicular to the substrate surface. For the polarization a Moxtec polarizer is used. The exposure energy of the polarised UVA light, using a Moxtec polariser, was 128 mJ·cm$^{-2}$. Then the sample was rotated 45° from starting position with a help of moving stage. The first zone of exposure was masked to keep the reference exposure results done at 0°. The rest of the substrate was irradiated with this same polarized UVA light with energy of 128 mJ·cm$^{-2}$. The formulation S2 (Example 26) is spin-coated at 800 rpm onto the substrate exposed with linearly polarised light, which is then dried for 30 seconds at 50° C. The resulting substrate is subsequently purged with nitrogen atmosphere for 30 seconds and then exposed with 1 J·cm$^{-2}$ of isotropic UV light under nitrogen atmosphere. The prepared device is placed under polarized microscope on rotating stage and the dark state of the first zone exposed with E1 is defined as reference (0°) position. The sample is next shifted to the zone exposed with E1(0°)+E2(45°), when E2=E1. The dark state position is found with the help of rotating stage. The angle difference between reference position and second position, i.e the deviation of azimuthal angle is measured and reported in the table below for the following photoreactive polymers.

The azimuthal stability is defined to be very good, if the deviation of azimuthal angle is below 6°. The azimuthal stability is defined to be good if the deviation of azimuthal angle is between 7° and 15°. The azimuthal stability is defined to be medium if the deviation of azimuthal angle is between 16° and 20° The azimuthal stability is defined to be bad if the deviation of azimuthal angle is above 21° The results are summarized in the below table.

| From examples | Azimuthal stability |
| --- | --- |
| 11O | Very good |
| 11B | Very good |
| 11A | Very good |
| 11E | Medium |
| 11R | Very good |
| 11I | Very good |
| 11M | Very good |
| 11N | Good |
| 11L | Very good |
| 11S | Very good |
| 11W | Good |
| 11Y | Good |
| 11AA | Very good |
| 11AB | Very good |

Example 30

Application of PAA-1 (Example 24) as Photoalignment Material for IPS Mode

A liquid crystal cell 1 is prepared, wherein the liquid crystal is aligned by photoreactive polyamic acid PAA-1 and the electric field is applied between two plan electrodes on each side of the cell gap.

A 4.0% solution of polyamic acid PAA-1 is prepared by mixing the solid polyamic acid PAA-1 in NMP and stirred thoroughly till the solid polyamic acid PAA-1 is dissolved and a second solvent butyl cellulose (BC) is added and the whole composition is stirred thoroughly to obtain final solution. The solvent ratio between NMP and butyl cellulose is 1:1. The above polymer solution was spin-coated onto the two ITO coated glass substrates at a spin speed of 1700 rpm for 30 seconds. After spin coating the substrates are subjected to baking procedure consisting of pre-baking for 1.5 minutes at 130° C. and post-baking for 40 minutes at a temperature of 200° C. The resulting layer thickness is around 70 nm. This substrate is exposed so that the angle between the direction of linearly polarized UV light (LPUV) and the direction of electrode stripes is 78°. The incidence angle of the LPUV, relative to the normal of the substrate surface, was 0°. The plane of polarization was within the plane spanned by the substrate normal and the propagation direction of the light. The applied exposure dose is 500 mJ/cm$^2$. After LPUV exposure a cell is assembled with the 2 substrates, the exposed polymer layers facing to the inside of the cell. The substrates are adjusted relative to each other such that the induced alignment directions are parallel to each other (corresponds to the anti-parallel, i.e 180°, rubbed configuration in case of alignment by rubbing procedure). The cell is capillary filled with liquid crystal MLC7067 (Merck KGA). After that, the cell is optionally annealed at about 92° C. for 10 minutes and slowly cooled down to room temperature. The liquid crystal in the cell showed well defined and homogeneous planar orientation after thermal annealing of the cell.

Example 31

Cells are prepared with PAA-1, PAA-2, PAA-3, PAA-4, PAA-7 as in Example 30. Alignment quality of the liquid crystal in the cell is checked by placing the cell between two crossed polarizers and adjusted to obtain dark state. The alignment quality is defined to be very good, if the dark state show no defects and the liquid crystal is very well oriented. The alignment quality is defined to be medium if the dark state has light leakage because of slight inhomogeneous orientation of liquid crystal in some areas of the cell. The alignment quality is defined to be worse, if liquid crystal is not oriented with absence of dark state. The contrast of cells were measured in the NB mode (crossed polarizers) using a white light source. The polarisers are rotated until a minimum transmission Tmin is measured, then the maximum transmission Tmax is determined between parallel polarizers.

Contrast Ratio=$T$max/$T$min

The results show high contrast values for cells made according to the present invention. The results are summarized in the Table below.

| Compound | Alignment quality | Contrast Ratio |
| --- | --- | --- |
| PAA-1 | Very good | 1750-1850 |
| PAA-2 | Very good | 1750-1850 |
| PAA-3 | Very good | 1650-1750 |
| PAA-4 | Very good | 1750-1850 |
| PAA-7 | Very good | 1600-1700 |

Example 32

Application as Photoalignment Material

Alignment layers are prepared as in Examples 27 except that materials from Example 12 to Example 17 are used and the substrates are subsequently irradiated with polarized UVB and UVA. The minimum energy needed to obtain a good alignment quality without defects in LCP film is determined for each compound. The azimuthal stability is also measured as in Example 29. The results are given in the following table.

| From examples | E min for orientation with UVA (mJ · cm$^2$) | E min for orientation with UVB (mJ · cm$^2$) | Azimuthal stability |
|---|---|---|---|
| 12 | 32 | 4 | Good |
| 13 | 12 | 4 | Good |
| 14 | 12 | 4 | Good |
| 15 | 16 | 4 | Medium |
| 16 | 8 | 4 | Good |

The invention claimed is:

1. Compound according to the general formula (I)

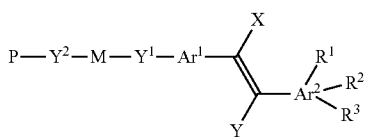

wherein
Ar$^1$ is phenylene which is unsubstituted;
Ar$^2$ is phenylene or biphenylene which is unsubstituted or substituted by R$^1$, R$^2$ and R$^3$;
and wherein:
if X is hydrogen and Y is CN,
then R$^1$, R$^2$ or R$^3$ are independently from each other hydrogen or —CF$_3$, with the proviso that R$^1$, R$^2$ or R$^3$ are not simultaneously hydrogen;
if X is CN and Y is hydrogen;
then R$^1$, R$^2$ or R$^3$ are independently from each other hydrogen or —CF$_3$;
M is a single covalent bond or a straight-chain or branched alkylene residue having 1, 2, 3, 4, 5, 6, 7, 8, 9, 10, 11, 12, 13, 14, 15 or 16 carbon atoms, which is unsubstituted, mono-substituted by cyano or halogen, or poly-substituted by halogen and wherein one or more, CH$_2$ groups independently may be replaced by a heteroatom or a group selected from —O—, —CO—O—, —O—CO—, —NR$^{1'}$—, —NR$^{1'}$—CO—, —CO—NR$^{1'}$—, —NR$^{1'}$—CO—O—, —O—CO—NR$^{1'}$—, —NR$^{1'}$—CO—NR$^{1'}$—, —C=C—, —C≡C—, —O—CO—O— and —Si(CH$_3$)$_2$—O—Si(CH$_3$)$_2$—, wherein R$^{1'}$ is a hydrogen atom or lower alkyl;
Y$^1$ is —O—;
Y$^2$ is single bond, —O—, —CO—, —COO— or —OCO—;
P is a hydrogen atom, optionally substituted alkyl, or a polymerizable group, which is selected from acrylate, methacrylate, vinyl ether and ester, epoxy, styrene derivatives, siloxanes, imide monomers, amic acid monomers and their corresponding polymers, homo or copolymers.

2. Oligomer, dendrimer or a polymer, which polymer is a copolymer or homopolymer, comprising at least one compound according to claim 1 as monomer unit.

3. Oligomer, dendrimer or a polymer, which polymer is a copolymer or homopolymer, according to claim 2 in form of a gel or a network.

4. Oligomer, dendrimer or a polymer, which polymer is a copolymer or homopolymer, according to claim 2 further comprising additives.

5. Oligomer, dendrimer or a polymer, which polymer is a copolymer of homopolymer according to claim 2 further comprising additives selected from the group consisting of silane-containing compounds, acrylate- or epoxy-containing crosslinking agents, a photosensitiser, a photoradical generator and/or a cationic photoinitiator.

6. Oligomer, dendrimer or a polymer, which polymer is a copolymer or homopolymer, according to claim 2 further comprising in admixture other polymers, oligomers, monomers, photoactive polymers, photoactive oligomers and/or photoactive monomers.

7. Oligomer, dendrimer or a polymer, which polymer is a copolymer or homopolymer, according to claim 2 which is applied to a support and crosslinked by irradiation with aligning light.

8. Composition comprising an oligomer, dendrimer or a polymer, which polymer is a copolymer or homopolymer, according to claim 2.

9. Composition comprising an oligomer, dendrimer or a polymer, which polymer is a copolymer or homopolymer, according to claim 3.

10. Composition comprising an oligomer, dendrimer or a polymer, which polymer is a copolymer or homopolymer, according to claim 4.

11. Composition comprising an oligomer, dendrimer or a polymer, which polymer is a copolymer or homopolymer, according to claim 5.

12. Composition comprising an oligomer, dendrimer or a polymer, which polymer is a copolymer or homopolymer, according to claim 6.

13. Composition comprising an oligomer, dendrimer or a polymer, which polymer is a copolymer or homopolymer, according to claim 7.

14. Method of using one or more oligomers, dendrimers or a polymer, which polymer is a copolymer or homopolymer, comprising forming an alignment layer for liquid crystals from one or more oligomers, dendrimers or a polymer, which polymer is a copolymer or homopolymer, according to claim 2.

15. Alignment layer comprising one or more oligomer, dendrimer or a polymer, which polymer is a copolymer or homopolymer, according to claim 2.

16. Alignment layer according to claim 15 having a pattern of different alignment directions.

17. Method for the preparation of an alignment layer, wherein one or more oligomers, dendrimers or a polymer, which polymer is a copolymer or homopolymer, according to claim 2 is applied to a support, which is optionally provided with an electrode, and optionally after prior imidisation, said applied oligomers, dendrimers or polymers are crosslinked by irradiation with aligning light.

18. Optical and electro-optical unstructured or structured constructional elements comprising at least one alignment layer according to claim 15.

* * * * *